United States Patent [19]

Bodor, Nicholas S.

[11] Patent Number: 4,880,816

[45] Date of Patent: * Nov. 14, 1989

[54] BRAIN-SPECIFIC DELIVERY OF DOPAMINE UTILIZING DIHYDROPYRIDINE/PYRIDINIUM SALT-TYPE REDOX CARRIERS

[75] Inventor: Bodor, Nicholas S., Gainesville, Fla.

[73] Assignee: University of Florida, Gainesville, Fla.

[*] Notice: The portion of the term of this patent subsequent to Sep. 10, 2002 has been disclaimed.

[21] Appl. No.: 116,583

[22] Filed: Nov. 4, 1987

Related U.S. Application Data

[60] Division of Ser. No. 733,463, May 13, 1985, Pat. No. 4,727,079, which is a continuation-in-part of Ser. No. 665,940, Oct. 29, 1984, Ser. No. 516,382, Jul. 22, 1983, Pat. No. 4,540,564, and Ser. No. 461,543, Jan. 27, 1983, which is a continuation-in-part of Ser. No. 379,316, May 18, 1982, Pat. No. 4,479,932, said Ser. No. 665,940, and Ser. No. 516,382, each is a continuation-in-part of Ser. No. 475,493, Mar. 15, 1983, Pat. No. 4,622,218, Ser. No. 461,543, and Ser. No. 379,316, said Ser. No. 665,940, is a continuation-in-part of Ser. No. 516,382.

[30] Foreign Application Priority Data

May 16, 1983 [CA] Canada ................................. 428192

[51] Int. Cl.$^4$ ................. C07D 213/56; C07D 215/54; A61K 31/44; A61K 31/47

[52] U.S. Cl. ..................................... 514/307; 514/311; 514/354; 514/355; 546/146; 546/165; 546/168; 546/316; 546/322; 546/323

[58] Field of Search ............... 546/146, 168, 165, 322, 546/323, 316; 514/307, 311, 354, 355

[56] References Cited

U.S. PATENT DOCUMENTS

| | | | |
|---|---|---|---|
| 3,962,447 | 6/1976 | Higuchi et al. | 514/89 |
| 4,035,507 | 7/1977 | Bodor et al. | 514/533 |
| 4,065,566 | 12/1977 | Bodor et al. | 514/333 |
| 4,540,564 | 9/1985 | Bodor | 424/9 |
| 4,727,079 | 2/1988 | Bodor | 514/307 |

OTHER PUBLICATIONS

Bodor et al, Science, vol. 214, No. 4527 (1981), pp. 1370–1372.
Bodor et al, J. Pharm. Sci., vol. 67, No. 5 (May 1978), pp. 685–687.
Chemical & Engineering News, Dec. 21, 1981, pp. 24–25.
Bodor et al, J. Med. Chem., vol. 26, Apr. 1983, pp. 528–534.
Bodor et al, J. Med. Chem., vol. 26, Mar. 1983, pp. 313–317.
Bodor, in Design of Biopharmaceutical Properties Through Prodrugs and Analogs, Roche, E. B. (ed.), APhA Academy of Pharm. Sci., Washington, DC, pp. 98–135 (1976).
The Friday Evening Post, Aug. 14, 1981, Health Center Communications, Gainesville, Florida.
Science News, Jan. 2, 1982, vol. 121, No. 1, p. 7.
Bodor et al, Pharmacology and Therapeutics, vol. 19, No. 3, pp. 337–386 (Apr. 1983).
Bodor et al, Science, vol. 221, Jul. 1983, pp. 65–67.
Simpkins et al, J. Pharm. Sci., vol. 74, No. 10 (Oct. 1985), pp. 1033–1036.

Primary Examiner—Alan L. Rotman
Attorney, Agent, or Firm—Mary Katherine Baumeister; Dennis P. Clarke

[57] ABSTRACT

A brain-specific dopaminergic response is elicited in a patient in need of such treatment, e.g., a patient afflicted with Parkinson's disease of hyperprolactinemia, by administering thereto a therapeutically effective amount of preferably catechol protected dopamine tethered to a reduced, blood-brain barrier penetrating lipoidal form [D-DHC] of a dihydropyridine⇌pyridinium salt type redox carrier, e.g., 1,4-dihydrotrigonelline. Oxidation of the dihydropyridine carrier moiety in vivo to the ionic pyridinium salt type dopamine/carrier entity [D-QC]+ prevents elimination thereof from the brain, while elimination from the general circulation is accelerated, resulting in significant and prolongedly sustained brain-specific dopaminergic activity.

21 Claims, 10 Drawing Sheets

BRAIN-SPECIFIC DELIVERY OF DOPAMINE UTILIZING DIHYDROPYRIDINE/PYRIDINIUM SALT-TYPE REDOX CARRIERS

CROSS-REFERENCE TO RELATED APPLICATIONS

This application is a division of application Ser. No. 733,463, filed May 13, 1985, now U.S. Pat. No. 4,727,079, which is a continuation-in-part of my earlier copending applications Ser. No. 461,543, filed Jan. 27, 1983; Ser. No. 516,382, filed July 22, 1983 now U.S. Pat. No. 4,540,564; and Ser. No. 665,940, filed Oct. 29, 1984. Parent Ser. No. 461,543 is itself a continuation-in-part of application Ser. No. 379,316, filed May 18, 1982, now U.S. Pat. No. 4,479,932. Parent Ser. No. 516,382 is itself a continuation-in-part of applications Ser. No. 379,316, filed May 18, 1982, now U.S. Pat. No. 4,479,932; Ser. No. 461,543, filed Jan. 27, 1983; and Ser. No. 475,493, filed Mar. 15, 1983 now U.S. Pat. No. 4,622,218. Parent Ser. No. 665,940 is itself a continuation-in-part of applications Ser. No. 379,316, filed May 18, 1982, now U.S. Pat. No. 4,479,932; Ser. No. 461,543, filed Jan. 27, 1983; Ser. No. 475,493, filed Mar. 15, 1983; and Ser. No. 516,382, filed July 22, 1983. All of said parent applications and all applications of which those parent applications are continuations-in-part are hereby expressly incorporated by reference herein in their entireties and relied upon.

FIELD OF THE INVENTION

The present invention relates to a dihydropyridine⇄pyridinium salt type of redox or chemical delivery sytem for the site-specific and/or sustained eliciting of a dopaminergic response in the brain. More especially, this invention relates to the discovery that the neurotransmitter dopamine, which has the structural formula

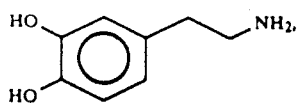

coupled to a lipoidal carrier moiety comprising a dihydropyridine nucleus, readily and easily penetrates the blood-brain barrier ("BBB") and attains increased levels of concentration in the brain; oxidation of the dihydropyridine carrier moiety in vivo to the ionic pyridinium salt prevents its elimination from the brain, while elimination from the general circulation is accelerated, and subsequent cleavage of the quaternary carrier/drug species at least in part results in sustained delivery of dopamine in the brain, or otherwise provides significant and prolongedly sustained brain-specific dopaminergic activity, with attendant facile elimination of the carrier moiety.

The topic chemical delivery system is well suited for the treatment of, e.g., Parkinsonism or hyperprolactinemia.

BACKGROUND OF THE INVENTION

In my aforenoted copending applications Ser. No. 516,382 and 665,940, as well as in their parent Ser. No. 379,316, detailed reference is made to the well established fact that the delivery of drug species to the brain is ofttimes seriously limited by transport and metabolism factors and, more specifically, by the functional barrier of the endothelial brain capillary wall deemed the blood-brain barrier or BBB. Site-specific delivery and sustained delivery of drugs to the brain are even more difficult, and to date (i.e. prior to the dates of applicant's earlier applications) no useful simple or generic techniques to achieve such phenomena are known to the art.

Previously, it has been suggested to deliver a drug species, specifically N-methylpyridinium-2-carbaldoxime chloride (2-PAM), into the brain, the active nucleus of which in and of itself constitutes a quaternary pyridinium salt, by way of the dihydropyridine latentiated prodrug form thereof. Such approach was conspicuously delimited to relatively small molecule quaternary pyridinium ring-containing drug species and did not provide the overall ideal result of brain-specific, sustained release of the desired drug, with concomitant rapid elimination from the general circulation, enhanced drug efficacy and decreased toxicity. Hence, no "trapping" in the brain of the 2-PAM formed in situ resulted, and obviously no brain-specific, sustained delivery occurred as any consequence thereof: the 2-PAM was eliminated as fast from the brain as it was from the general circulation and other organs. Compare U.S. Pat. Nos. 3,929,813 and 3,962,447; Bodor et al, J. Pharm. Sci., 67, No. 5, pp. 685–687 (1978); Bodor et al, Science, Vol. 190 (1975), pp. 155–156; Shek, Higuchi and Bodor, J. Med. Chem., Vol. 19 (1976), pp. 113–117. A more recent extension of this approach is described by Brewster, Dissertation Abstracts International, Vol. 43, No. 09, March 1983, p. 2910B.

It has also previously been speculated to deliver, e.g., an antitumor agent, into the brain by utilizing a dihydropyridine/pyridinium redox carrier moiety therefor, but this particular hypothesis necessarily entails derivatizing the dihydropyridine/pyridinium carrier with a substituent itself critically designed to control the release rate of the active drug species from the quaternary derivative thereof, as well as being critically functionally coordinated with the particular chemical and therapeutic activity/nature of the antitumor drug species itself; Bodor et al, J. Pharm. Sci., supra. See also Bodor, "Novel Approaches for the Design of Membrane Transport Properties of Drugs", in Design of Biopharmaceutical Properties Through Prodrugs and Analogs, Roche, E. G. (ed.), APhA Academy of Pharmaceutical Sciences, Washington, D.C., pp. 98–135 (1976). Moreover, the hypothesis does not include any indication of what chemical transformations would be needed to link any specific antitumor agent (or indeed any specific drug) to an appropriate carrier moiety.

Accordingly, acutely serious need exists in this art for a truly effective generic but nonetheless flexible method for the site-specific, or sustained delivery, or both, or drug species to the brain, while at the same time avoiding the aforesaid noted and notable disadvantages and drawbacks associated with penetration of the blood-brain barrier, with dihydropyridine latentiated prodrug forms of drug species themselves comprising a pyridinium salt active nucleus, and with the necessity for introducing critically coordinated and designed, release rate-controlling substituents onto any particular drug/carrier moiety. This need has been addressed by applicant's earlier applications referred to hereinabove, and especially by the Ser. Nos. 379,316, 516,382 and 665,940. Thus, a major object of the invention disclosed and claimed in my '316, '382 and '940 applications is the provision of just such a generic method for the site-specific/sustained delivery of centrally acting drug species to the brain, by administering to a patient in need of such treatment an effective amount of the target drug species [D] tethered to a reduced, blood-brain barrier penetrating lipoidal form [DHC] of a dihydropyridine⇌pyridinium salt type redox carrier. Oxidation of the dihydropyridine carrier moiety in vivo to the ionic pyridinium salt type drug/carrier entity [D-QC]+ prevents elimination thereof from the brain, while elimination from the general circulation is accelerated, and subsequent cleavage of the quaternary carrier/drug species results in sustained delivery of the drug [D] in the brain and facile elimination of the carrier moiety [QC]+.

Another object of said '316, '382 and '940 invention is to provide for brain-specific drug delivery utilizing a dihydropyridine⇌pyridinium salt carrier type redox system, which drug/carrier system is characterized by enhanced drug efficacy and decreased toxicity. Indeed, consistent therewith systemic toxicity is significantly reduced by accelerating the elimination of the drug/quaternary carrier system, and even central toxicity is reduced by providing a low level, sustained release of the active drug species in the brain.

In capsule summary, my '316, '382 and '940 invention features a dihydropyridine⇌pyridinium salt carrier redox system for the specific and sustained delivery of drug species to the brain according to the following Scheme 1:

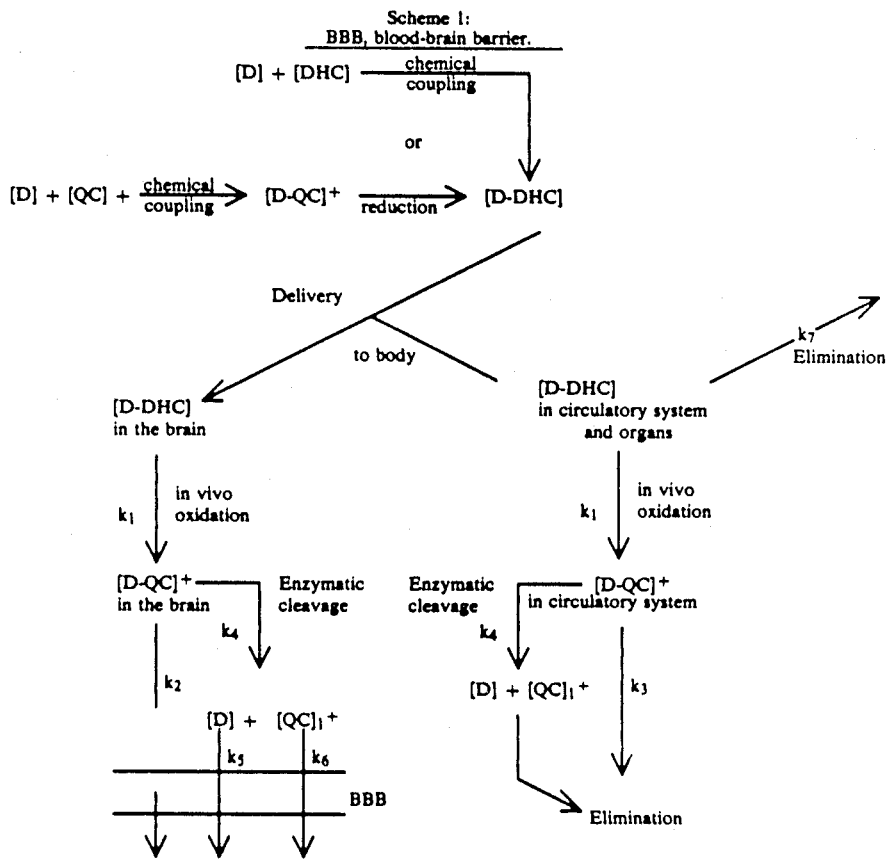

Consistent with the foregoing Scheme 1, any drug species [D] is coupled to a quaternary pyridinium salt carrier [QC]+ and the prodrug [D-QC]+ which results is then reduced chemically to the lipoidal dihydro proprodrug form [D-DHC]. Alternatively, the drug species [D] can be directly coupled to the dihydro carrier [DHC] in certain instances to yield said pro-prodrug form [D-DHC]. After administration of the [D-DHC] in vivo, it is rapidly distributed throughout the body, including the brain. The dihydro form [D-DHC] is then in situ oxidized (rate constant, $k_1$) (by the NAD⇌NADH coenzyme system) to the ideally inactive original [D-QC]+ quaternary salt prodrug, which, because of its ionic, hydrophilic character, is rapidly eliminated from the general circulation of the body, while the blood-brain barrier prevents its elimination from the brain ($k_3 \gg k_2$; $k_3 \gg k_7$). Enzymatic cleavage of the

[D-QC]+ that is "locked" in the brain effects a sustained delivery of the drug species [D], followed by its normal elimination ($k_5$), metabolism. A properly selected carrier [QC]+ will also be rapidly eliminated from the brain ($k_6 >> k_2$). Because of the facile elimination of [D-QC] from the general circulation, only minor amounts of drug are released in the body ($k_3 >> k_4$); [D] is released primarily in the brain ($k_4 > k_2$). The overall result is a brain-specific, sustained release of the target drug species. Cf. Bodor et al, Science, Vol. 214, Dec. 18, 1981, pp. 1370-1372; The Friday Evening Post. Aug. 14, 1981, Health Center Communications, University of Florida, Gainesville, Fla.; Chemical & Engineering News, Dec. 21, 1981, pp. 24-25; Science News, Jan. 2, 1982, Vol. 121, No. 1, page 7. See also Bodor er al, J. Med. Chem., Vol. 26, March 1983, pp. 313-317; Bodor et al, J. Med. Chem., Vol. 26, April 1983, pp. 528-534; Bodor et al, Pharmacology and Therapeutics, Vol. 19, No. 3, pp. 337-386 (April 1983); Bodor et al, Science, Vol. 221, July 1983, pp. 65-67; and Bodor et al, J. Pharm. Sci., Vol. 73, No. 3, March 1984, pp. 385-388.

It is known to this art that Parkinsonism, a striatal dopamine deficiency syndrome [H. Ehringer and O. Hornykiewicz, Klin. Wsch., 38, 1236 (1960)], cannot be treated directly with dopamine, for dopamine and related catecholamines also do not cross the blood-brain barrier [B. E. Roos and G. Steg, Life Sci., 3, 351 (1964)]. L-Dopa, considered as a prodrug for dopamine, was first discovered to be useful in the treatment of Parkinsonism more than twenty years ago [A. Barbeau, Excepta Medica, Int. Congr. Ser., 38, 152 (1961); W. Birkmayer and O. Hornykiewicz, Wien. Klin. Wochenschr., 73, 787 (1961)]. Indeed, L-Dopa is considered to be the best available treatment for Parkinsonism, but, unfortunately, at the expense of a wide variety of undesirable side effects [A. Barbeau, TIPS, 2 (11), 297 (1981)]. The peripheral side effects of L-Dopa, which range from nausea and vomiting to cardiac arrythmias and hypotension, appear to be due to one or more of the metabolic products thereof, rather than L-Dopa per se. L-Aromatic amino acid decarboxylase enzyme is responsible for the major metabolism of L-Dopa, whether prior, during or after absorption. Concurrent administration of L-Dopa with an inhibitor of aromatic amino acid decarboxylase, which should not be able to penetrate the BBB, reduces the decarboxylation of L-Dopa in peripheral tissues. Such reduction allows higher proportions of L-Dopa to reach the CNS and at the same time diminishes the peripheral side effects considerably, particularly vomiting and cardiac arrythmias, but a number of serious side effects still persist [A. Barbeau, TIPS, supra; A. Barbeau and M. Roy, Neurology, 26, 399 (1976)]. Attempts have also been made to alleviate the well-known dissolution, absorption and metabolism problems of L-Dopa [H. Ninterberger, Biochem. Med., 5, 412 (1971); H. Shindo, T. Komai, K. Tanaka, E. Nakajima and N. Miyakoshi, Chem. Pharm. Bull., 21, 826 (1973); C. O. Rutledge and M. M. Hoehn, Nature (London), 244, 447 (1973); R. L. Bronaugh, R. J. McMurty, M. M. Hoehn and C. O. Rutledge, Biochem. Pharmacol., 24, 1317 (1975)], employing prodrug approaches [N. Bodor, K. B. Sloan, T. Higuchi and K. Sasahara, J. Med. Chem., 20, 1435 (1977); A. M. Felix, D. P. Winter, S. S. Wang, I. D. Kulesha, W. R. Pool, D. L. Hane and H. Sheppard, J. Med. Chem., 17, 422 (1974)].

Additionally, dopamine agonists, which are used in the treatment of hyperprolactinemia associated with pituitary adenomas or amenorrhea [R. F. Spark and G. Dickenstein, Ann. Int. Med., 90, 949 (1979)], also induce unwanted side effects. The use of dopamine agonists in the treatment of hyperprolactinemia is based on the ability of these compounds to supress the production of prolactin. While the incidence of hyperprolactinemia in the general population is difficult to determine, it has been estimated that hyper-prolactinemia is the most frequency endocrine disease and represents 10% of all such disorders [Riskin et al, "Management of Pituitary Secretory Adenomas", in Harrison's Updates on Internal Medicine, Vol. 3, eds. K. J. Isselbacher, R. D. Adams, E. Braunwald, J. B. Martin, R. G. Peterodorf and J. W. Wilson, McGraw-Hill Publishing Co., New York, 235-252 (1982)]. Hyperprolactinemia can be caused by micro- or macro-adenomas of the anterior pituitary gland (Post et al, The Pituitary Adenoma, Plenum Publishing Co., New York. 1980); by defects in the tuberoinfundibular dopamine system, which tonically inhibits prolactin secretion [MacLeod et al, "Regulation of the Synthesis and Release of Prolactin", in Lactogenic Hormones, eds. G. E. W. Wolstenholme and J. Knight, Churchill Livingstone Press, Edenburgh, England, 53 (1972)]; by chronic excessive estrogen exposure [Ben-Jonathan et al, Endocrinology, 106, 690 (1980)]; or by defects within the anterior pituitary gland itself. Additionally, hyperprolactinemia can occur during and after chronic use of oral contraceptives and therapy with neuroleptics [Riskin et al, supra; Fluckiger, "Pharmacology of Prolactin Secretion", in Treatment of Pituitary Adenomas, eds. R. Fahlbusch and K. V. Werder, PSG Publishing Co., Stuttgart, Germany, 351-360 (1978)]. Interestingly, the most common hyperprolactinemia occurs physiologically during late gestation and in response to the suckling stimulus (MacLeod et al, supra).

Costello [Am. J. Phathol. 12, 205-216 (1936)] observed nearly 50 years ago that 22.5% of anterior pituitaries obtained from unselected autopsies had adenomas. This astonishing finding was given little credence until very recently when several studies observed an incidence of pituitary tumors of 4.8 to 27%, with most frequent incidence being 22.5 to 27% [Costello, supra; Gold, Epidemiol. Rev. 3, 163-183 (1981); Bloodworth et al, "Electron Microscopy of Pituitary Tumors", in Recent Advances in the Diagnosis and Treatment of Pituitary Tumors, ed. J. A. Linfood, Raven Press, New York, 1-159 (1979); McComb et al, Arch. Phathol. Lab. Med., 107, 488-491 (1983)]. Thus, it is reasonable to assume that approximately 25% of the general population has pituitary adenomas. The incidence of anterior pituitary tumors is much more frequent in women than men. Peak incidence occurs between the ages of 30 and 60 [Karduck et al, "Transmaxillar-Transsphenoidal Hypophysectomy: Approach and Rhinological Followup", in Treatment of Pituitary Adenomas", eds. R. Fahlbusch and K. V. Werder, PSG Publishing Co., Stuttgart, Germany, 299-304 (1978)].

With the advent of immunohistochemical methods to define the hormonal type of anterior pituitary tumors, it has been determined that 40 to 70% of these adenomas secrete prolactin [Post et al, supra; McComb et al, supra; Hardy, in Pituitary Microadenomas, eds. G. Faglia, M. A. Giovanelli and R. M. MacLeod, Academic Press, London, p. 7 (1980); Lancranjan, "Increasing Use of Dopamine Agonists as the First Choice Therapy of Prolactin-secreting Adenomas", in A Clinical Problem: Microadenoma Diagnosis and Treatment, ed. G. M. Molinatti, Excerpta Medica Press, Amsterdam, 103-113 (1982); and many others]. The presence of this high incidence suggests that prolactin secreting cells are more susceptible than other pituitary cell types to neoplastic transformation. Additionally, hyperprolactinemia is associated in 30 to 40% of cases with growth hormone-secreting tumors [Cocchi et al, "Pathophysiological Aspects of Prolactinomas", in A Clinical Problem: Microadenoma Diagnosis and Treatment, ed. G. M. Molinatti, Excerpta Medica Press, Amsterdam, 1-15 (1982)]. If one assumes that 25% of the general population has pituitary microadenomas and of these 50% are prolactinomas, then about 12.5% of the general population has prolactin-secreting microadenomas. Thus, in the United States alone, approximately 27.5 million people are in potential need of therapy for prolactinomas.

That 27.5 million people are not treated for anterior pituitary tumors is due to the fact that pituitary adenomas are diagnosed primarily from consequential reproduction problems. In women, microademonas and resulting hyperprolactinemia are frequently associated with secondary amenorrhea or galactorrhea. Up to 25% of women with secondary amenorrhea have causative hyperprolactinemia, while 30 to 90% of those with galactorrhea have chronically elevated serum prolactin [Schlechte et al, Endocrine Rev. 1, 295-308 (1980)]. In men, hyperprolactinemia is less common and is found in less than 8% of men with sexual impotence and in less than 4% of men with infertility [Millins, in Advances in Prolactin, eds. M. L'Hermite and S. L. Judd, Progress in Reproductive Biology, Volume 6, Basal Karger, p. 194). When pituitary adenomas increase in size, neurological signs such as headaches and visual field impairments occur.

While the primary treatment of macroadenomas is transsphenoidal surgery and radiotherapy, the recommended treatment for the more common microadenoma is controversial. Total removal of microadenomas is possible in up to 90% of cases with transsphenoidal surgery and menses returns in up to 75% of women and fertility is restored in 60 to 70% [Hordy, Clin. Neurosurg. 16, 185-217 (1969); Post et al, Amer. Med. Assoc. 242, 158-162 (1979); Tindall et al, J. Neurosurg. 48, 849-860 (1978)]. In women in whom menses and/or fertility does not return after surgery, bromocriptine therapy is usually effective [Zervas et at, New Eng. J. Med. 302, 210-214 (1980)]. In this regard, evidence for a normalization of serum prolactin levels with bromocriptine in 85% of women with microadenomas [Lancranjan, supra; Besser et al, Postgrad. Med 52 (Suppl. 1), 64 (1976); Friesen, in Ergot Compounds and Brain Function, eds. M. Goldstein, D. B. Calve, A. Lieberman and M. O. Thorner, Raven Press, New York, p. 147 (1980); Thorner et al, in Ergot Compounds and Brain Function, eds. M. Goldstein, D. B. Calve, A. Lieberman and M. O. Thorner, Raven Press, New York, p. 165 (1980)] and recent evidence that bromocriptine and other dopamine agonists reduced the size of tumors in 126 of 258 cases [Lancranjan, supra; Corenblum, Lancet 2, 786 (1978)], suggests the usefulness of dopaminergic agents in the non-surgical management of microadenomas.

An additional use of bromocriptine is post-partum prolactin reduction in women who choose not to nurse their newborns. Also, 1% of women who use oral contraceptives fail to resume normal cycles upon cessation of contraceptive use; these women are almost invariably hyperproplactinemic and can be effectively treated with bromocriptine or other dopaminergic drugs.

Thus, especially actuely serious need exists in this art to deliver a dopaminergic agent directly and specifically to the brain, in a sustained manner, and there elicit the desired dopaminergic response, e.g., for the treatment of Parkinsonism or hyperprolactinemia. This need has been addressed by applicant's earlier applications referred to above, and especially by the Ser. No. 461,543, and is also addressed by the present application.

SUMMARY OF THE INVENTION

It has now been found, and which constitutes a major object of this invention (as well as of my earlier copending applications Ser. No. 516,382, Ser. No. 665,940 and most especially Ser. No. 461,543), that my novel chemical delivery system based upon a dihydropyridine⇌pyridinium salt type redox carrier per my application Ser. No. 379,316, is uniquely well suited for the design of an effective dopamine chemical delivery system, for the site-specific and/or sustained eliciting of a significant dopaminergic response in the brain. In one aspect, the present invention thus provides, as an effective dopaminergic chemical delivery system, compounds having the formula

[D-DHC]   (I)

and non-toxic pharmaceutically acceptable salts thereof, wherein [D] is a dopamine having the structural formula

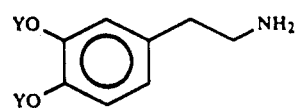

in which each Y is independently hydrogen or a hydrolytically or metabolically cleavable hydroxyl protective group, and [DHC] is the reduced, biooxidizable, blood-brain barrier penetrating, lipoidal form of a dihydropyridine⇌pyridinium salt redox carrier. In another aspect, the present invention provides compounds having the formula $$[D\text{-}QC]^+X^- \qquad (II)$$

wherein $X^-$ is the anion of a non-toxic pharmaceutically acceptable acid, [D] is a dopamine having the structural formula

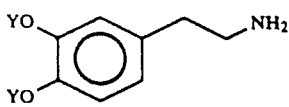

in which each Y is independently hydrogen or a hydrolytically or metabolically cleavable hydroxyl protective group, and $[QC]^+$ is the hydrophilic, ionic pyridinium salt form of a dihydropyridine⇌pyridinium salt redox carrier.

Briefly, one presently preferred chemical delivery system for dopamine according to this invention has the structure 2 in the following Scheme 2, wherein the amino function of dopamine is appropriately linked to the dihydropyridine-type carrier system, while the catechol function is advantageously protected, for example, as a corresponding ester function, e.g., the dipivalyl ester illustrated. The brain-specific delivery of dopamine, or the otherwise eliciting of a dopaminergic response, requires a succession of process, including oxidation of the dihydropyridine ring to the corresponding pyridinium salt (for example, structure 3), which provides the basis for "locking-in" the brain the molecule, hydrolysis of the, e.g., pivalyl esters (see structure 4) likely via the 3- and/or 4-monopivalyl esters and, finally, the release of dopamine 1 from 4, which can be either a hydrolysis or a reductive process [a possible reductive release of dopamine was very recently suggested by a model for a presynaptic terminal, L. L. Miller, A. N. K. Lau and E. K. Miller, J. Am. Chem. Soc., 104 5242 (1982)].

Scheme 2

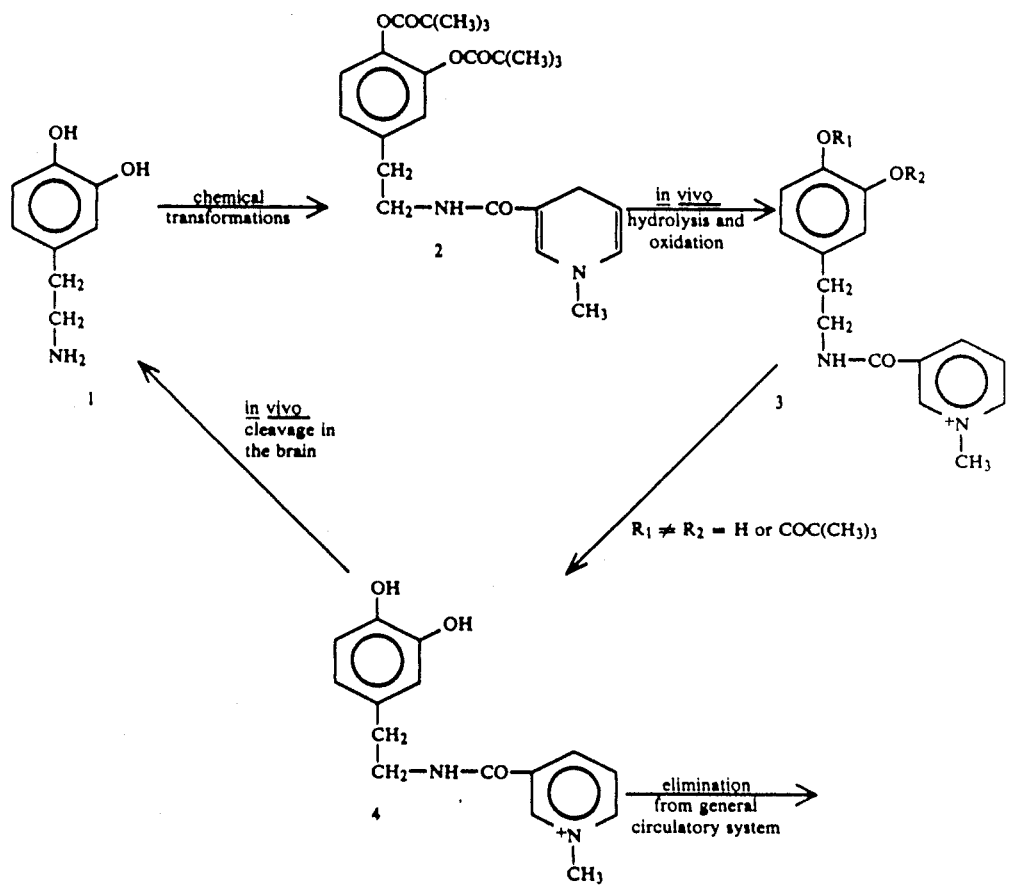

As per the above Scheme 2, for the brain specific delivery of dopamine 1, structure 2 is one chemical delivery system consistent herewith, and 4 is one precursor locked in the brain and eliminated rapidly from the rest of the body. Structures 3 depict intermediates formed during the stepwise hydrolysis and oxidation processes.

DETAILED DESCRIPTION OF THE INVENTION

Figure 1:
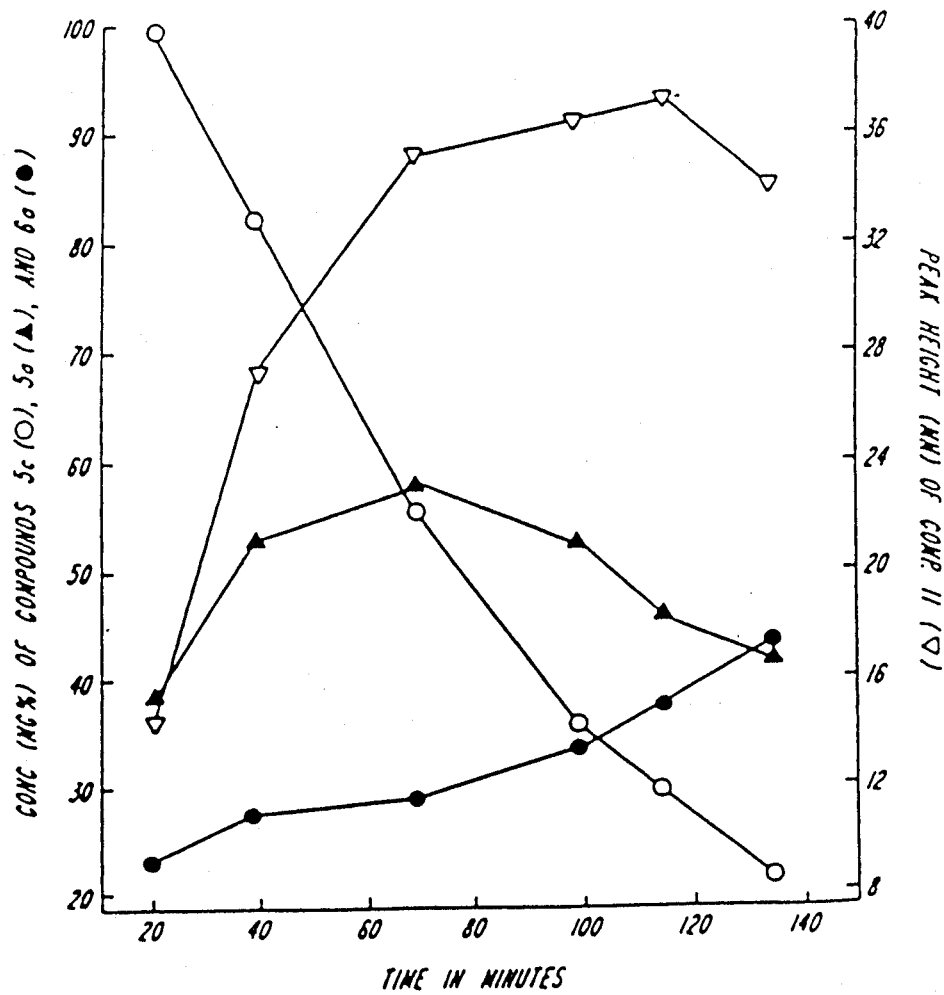
FIG. 1 is a graph plotting the time couse of 1-methyl-3-{N-[β-(3,4-dipivalyloxyphenyl)ethyl]}-carbamoyl-1,4-dihyropyridine 5c ⊖ and its products, the monopivalyl-dihydro derivative 11 (∇), the dihydrodopamine derivative 5a (▲) and the quaternary dopamine precursor 6a (●) in plasma.
Figure 2:
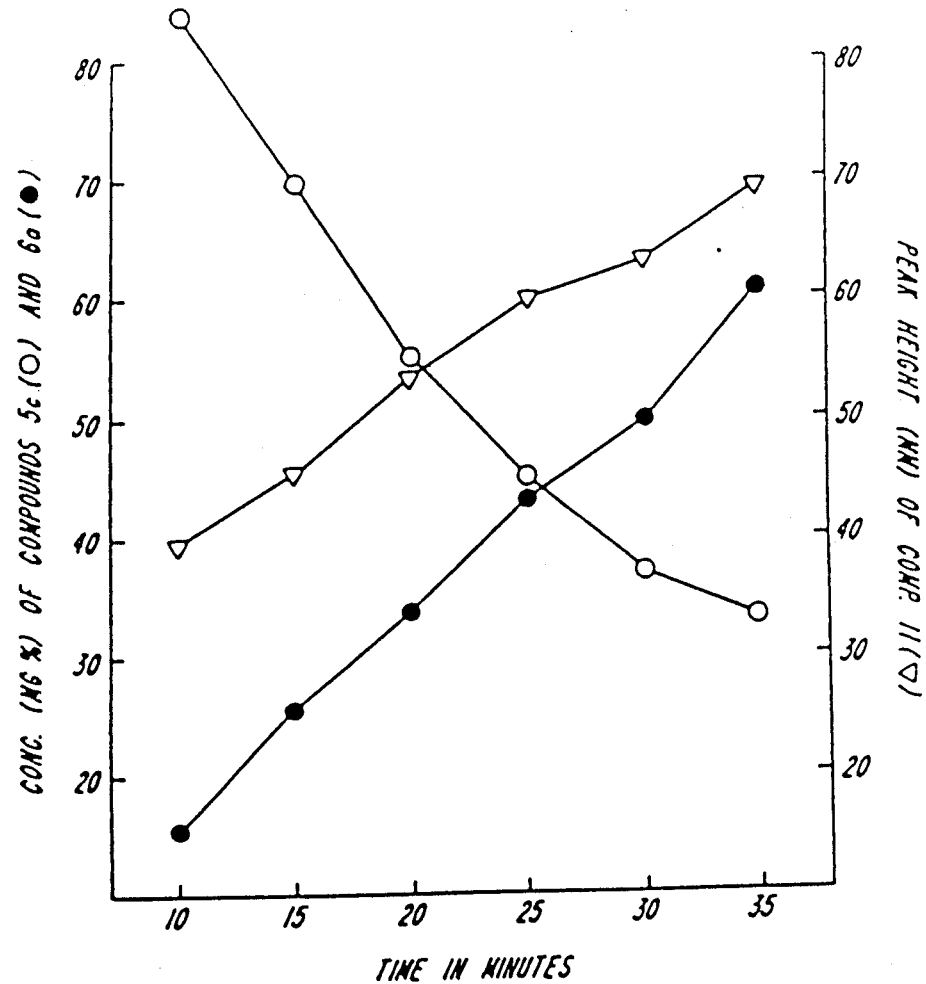
FIG. 2 is a graph plotting the time course of 1-methyl-3-{N-[β-(3,4-dipivalyloxyphenyl)ethyl]}-carbamoyl-1,4-dihydropyridine 5c ⊖ and its products, the monopivalyl-dihydro derivative 11 (▽) and the quaternary dopamine precursor 6a (●) in whole blood.
Figure 3:
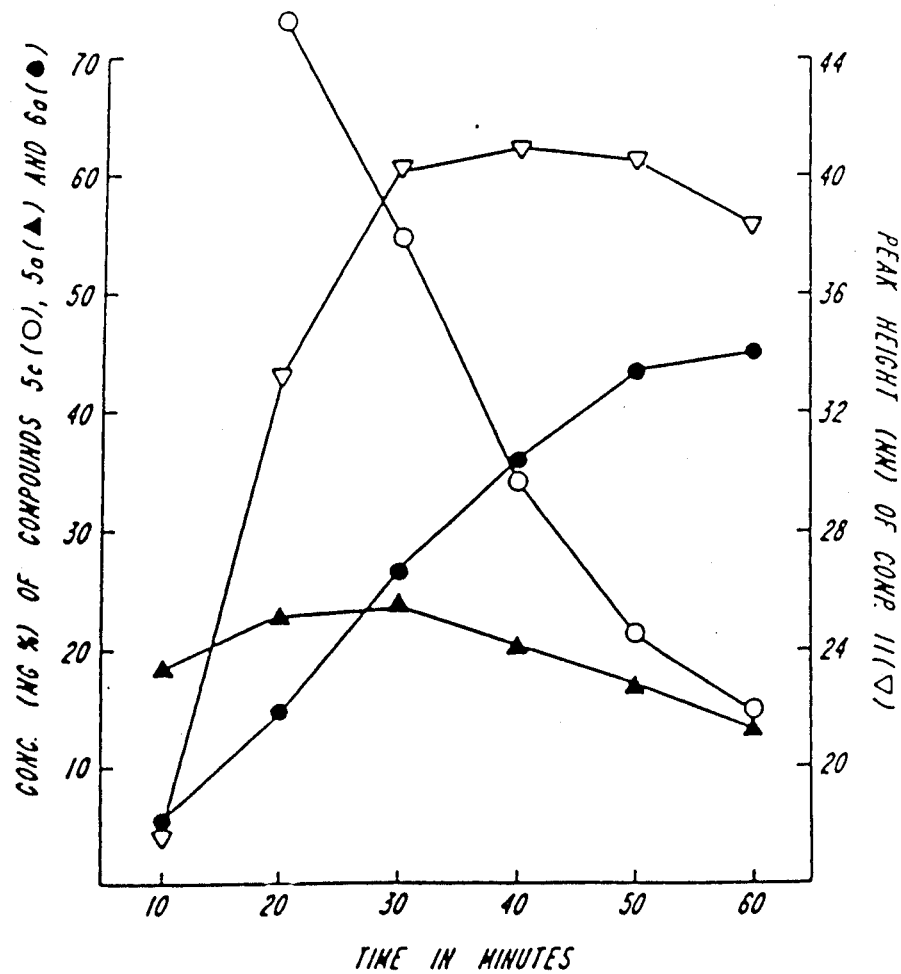
FIG. 3 is a graph plotting the time course of 1-methyl-3-{N-[β-(3,4-dipivalyloxyphenyl)ethyl]}-carbamoyl-1,4-dihydropyridine 5c ⊖ and its products, the monopivalyl-dihydro derivative 11 (▽), the dihydrodopamine derivative 5a (▲) and the quaternary dopamine precursor 6a (●) in 20% brain homogenate.
Figure 4:
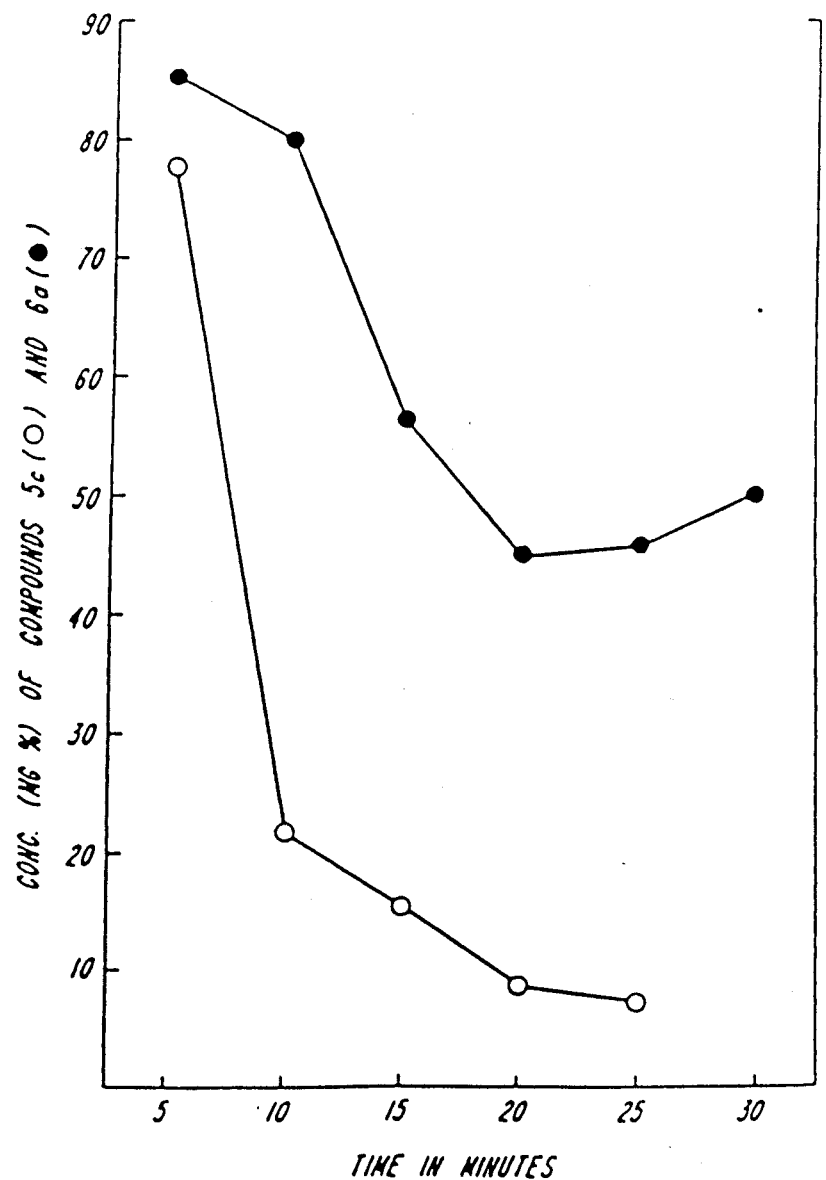
FIG. 4 is a graph plotting the time course of 1-methyl-3-{N-[β-(3,4-dipivalyloxyphenyl)ethyl]}-carbamoyl-1,4-dihydropyridine 5c ⊖ and its product, the quaternary dopamine precursor 6a (●) in 20% liver homogenate.

More particularly in accord with the present invention, the following definitions are applicable:

The term "lipoidal" as used herein is intended to designate a carrier moiety which is lipid-soluble or lipophilic.

The expression "hydroxyl protective group" is intended to designate a group which is inserted in place of the hydrogen atom(s) of an OH group or groups in order to prevent premature metabolism of said OH group or groups to the active form prior to the compound's reaching the desired site in the body. Typical hydroxyl protective groups contemplated by the present invention as possible values for Y are acyl groups and carbonates.

When the hydroxyl protective group is acyl (i.e., when it is an organic radical derived from a carboxylic acid by removal of the hydroxyl group), it preferably represents an acyl radical selected from the group consisting of alkanoyl having 2 to 8 carbon atoms; alkenoyl having one or two double bonds and 3 to 8 carbon atoms;

wherein the cycloalkyl portion contains 3 to 7 ring atoms and r is zero, one, two or three; phenoxyacetyl; pyridinecarbonyl; and

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, acetyl, propionyl, butyryl, isobutryl, valeryl, isovaleryl, 2-methylbutanoyl, pivalyl (pivaloyl), 3-methylpentanoyl, 3,3-dimethylbutanoyl, 2,2-dimethylpentanoyl and the like. Pivalyl, isobutyryl and isovaleryl are especially preferred.

When the acyl group is alkenoyl, there are included, for example, crotonyl, 2,5-hexadienoyl and 3,6-octadienoyl.

When the acyl group is

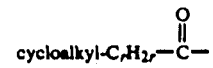

there are included cycloalkanecarbonyl and cycloalkanealkanoyl groups wherein the cycloalkane portion can optionally bear 1 or 2 alkyl groups as substituents, e.g. cyclopropanecarbonyl, 1-methylcyclopropanecarbonyl, cyclopropaneacetyl, α-methylcyclopropaneacetyl, 1-methylcyclopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cyclohexanecarbonyl, cycloheptanecarbonyl and cycloheptanepropionyl. Cyclohexanecarbonyl is especially preferred.

When the acyl group is pyridinecarbonyl, there are included picolinoyl (2-pyridinecarbonyl), nicotinoyl (3-pyridinecarbonyl) and isonicotinoyl (4-pyridinecarbonyl).

When the acyl group is

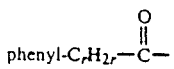

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β-(p-ethylphenyl)propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, p-n-butoxybenzoyl, 2,4,6-triethoxybenzoyl, 3,4-diethoxyphenylacetyl, β-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)benzoyl, m-trifluoromethylphenylacetyl, β-(p-trifluoromethylphenyl)propionyl, 2-methyl-4-methoxybenzoyl, 3-chloro-4-ethoxybenzoyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl and p-acetamidophenylpropionyl.

When the hydroxyl protective group is a carbonate grouping, it has the structural formula

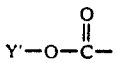

i.e., it is an organic radical which can be considered to be derived from a carbonic acid by removal of the hydroxyl group from the COOH portion. Y' preferably represents alkyl having 1 to 7 carbon atoms; alkenyl having one or two double bonds and 2 to 7 carbon atoms;

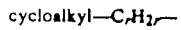

wherein the cycloalkyl portion contains 3 to 7 ring atoms and r is zero, one, two or three; phenoxy; 2-, 3- or 4-pyridyl; or

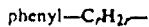

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is $C_1$-$C_7$ alkyl, particularly ethyl or isopropyl.

The expression "non-toxic pharmaceutically acceptable salts" as used herein generally includes the non-toxic salts of compounds of formula (I) of the invention formed with nontoxic, pharmaceutically acceptable inorganic or organic acids HX. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, toluenesulfonic and the like. The expression "anion of a non-toxic pharmaceutically acceptable acid" as used herein, e.g. in connection with structure (II), is intended to include anions of such inorganic or organic acids HX.

In accord with the present invention, the sustained delivery of dopamine to the brain in pharmacologically effective concentrations has now been demonstrated, paralleled with much lower concentrations in the peripheral circulation and other tissues, utilizing a trigonelline-type carrier system, with the catechol moiety thereof in certain instances being acylated. According to Scheme 3 which follows, one specific delivery sytem for dopamine, compound 5, on administration (e.g., by injection) is distributed throughout the body and by reason of its lipophilic character facilely penetrates the blood-brain barrier and enters the CNS. Following oxidation both in the brain and in the other tissues, the corresponding hydrophilic quaternary salt 6 is formed. The quaternary salt 6 is essentially "locked in" the brain and its concentration is considered to increase with time until reaching a maximum, which depends primarily on the relative rates of entrance of the dihydro compound 5 to the brain ($K_1$) as compared to $K_2$ to the other tissues, the rate of oxidation of the dihydro form to the quaternary ($K_3$ and $K_7$) and the rates of its disappearance from the brain ($K_4 + K_5$). At the same time, the very water soluble quaternary form(s) 6 is/are excreted readily via the kidney and the liver ($K_8 > K_4$). Derivatives 6 are considered to be essentially inactive forms ($K_8 > K_9$), and thus systemic activity/toxicity is minimized. Hence, the concentration of 5 and 6 in the blood rapidly increases. The ratio of the quaternary salt 6 in the brain relative to the blood increases to the point where 6, or metabolites thereof, can only be found in the brain. The quaternary 6, whether in the brain, blood or other tissues, is deemed to release dopamine and the non-toxic compound, trigonelline, depending upon the rates of site-specific conversion of the precursor 6 to the drug at each of these sites. The concentration of any released dopamine at any time is much higher in the brain than in the blood or other tissues. Also, as the enzymatic transformation of the quaternary precursor 6 to the drug (dopamine) is relatively slow, same permits a sustained release of dopamine. Too, the simultaneous protection/lipophilic derivatization of the catechol system in dopamine has also new been demonstrated.

It will be appreciated that a compound of formula (I), such as compound 5, may be administered as the free base, e.g. as depicted in Scheme 3, or in the form of a non-toxic pharmaceutically acceptable salt thereof, i.e., a salt which can be represented generally by the formula

[D—DHC].HX and more specifically with respect to Scheme 3 by the formula

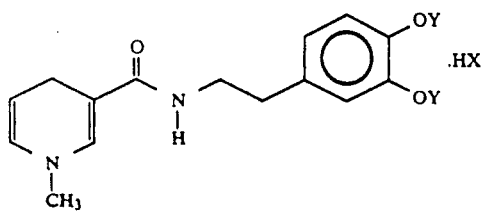

mula (II), i.e. salt of the compound 6 type, the anion X⁻ being an anion present in vivo. It is not necessary that the anion be introduced as part of the compound administered. And even when the compound of formula (I) (e.g. compound 5) is used in its salt form, the anion of the formula (II) compound (e.g. of compound 6) is not necessarily the same as that present in the formula (I) compound. In any event, the exact identity of the anionic portion of the compound of formula (II) such as compound 6 is immaterial to the in vivo transformation of (I) to (II), e.g. the depicted enzymatic transformation.

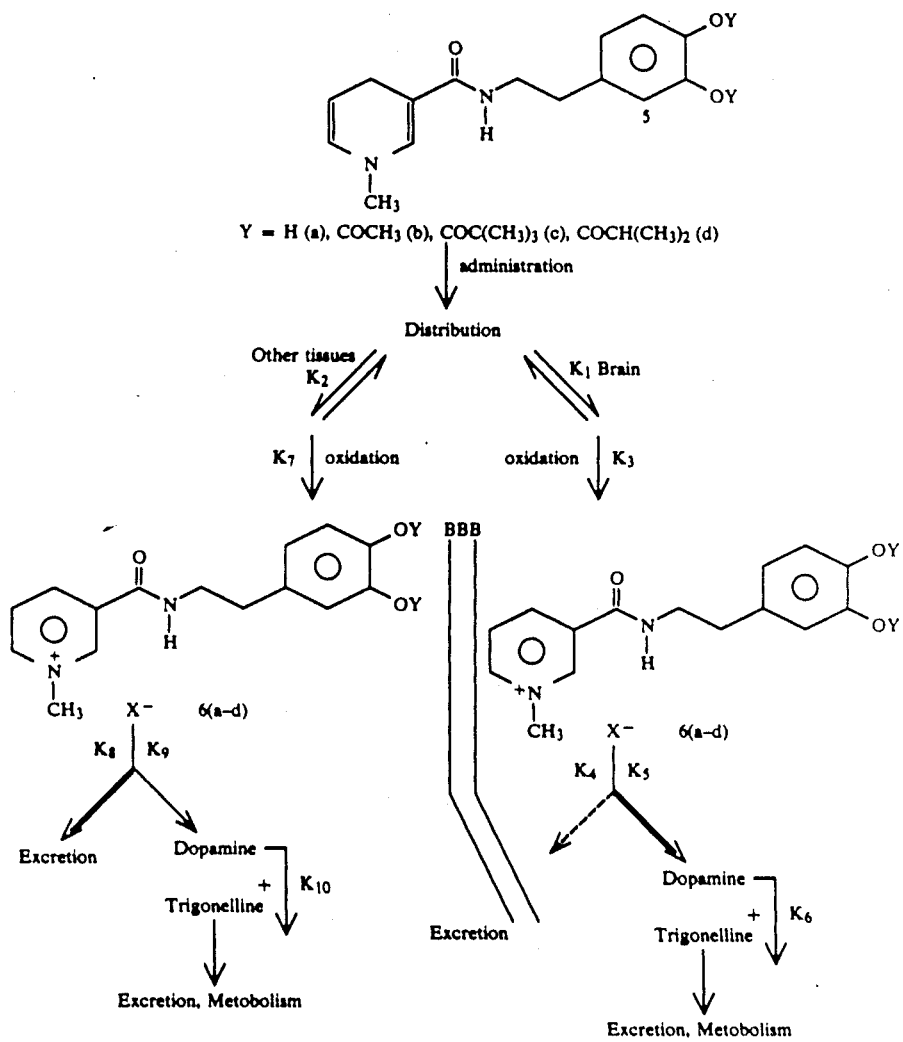

(Y is defined as in Scheme 3)
wherein HX is as defined before; and that, regardless of the actual form in which the compound is administered, it will be converted in vivo to a quaternary salt of for- With specific reference to the immediately above, the 1,4-dihydropyridine derivatives 5 were prepared as in the following Schemes 4, 5 and 6:

Scheme 4
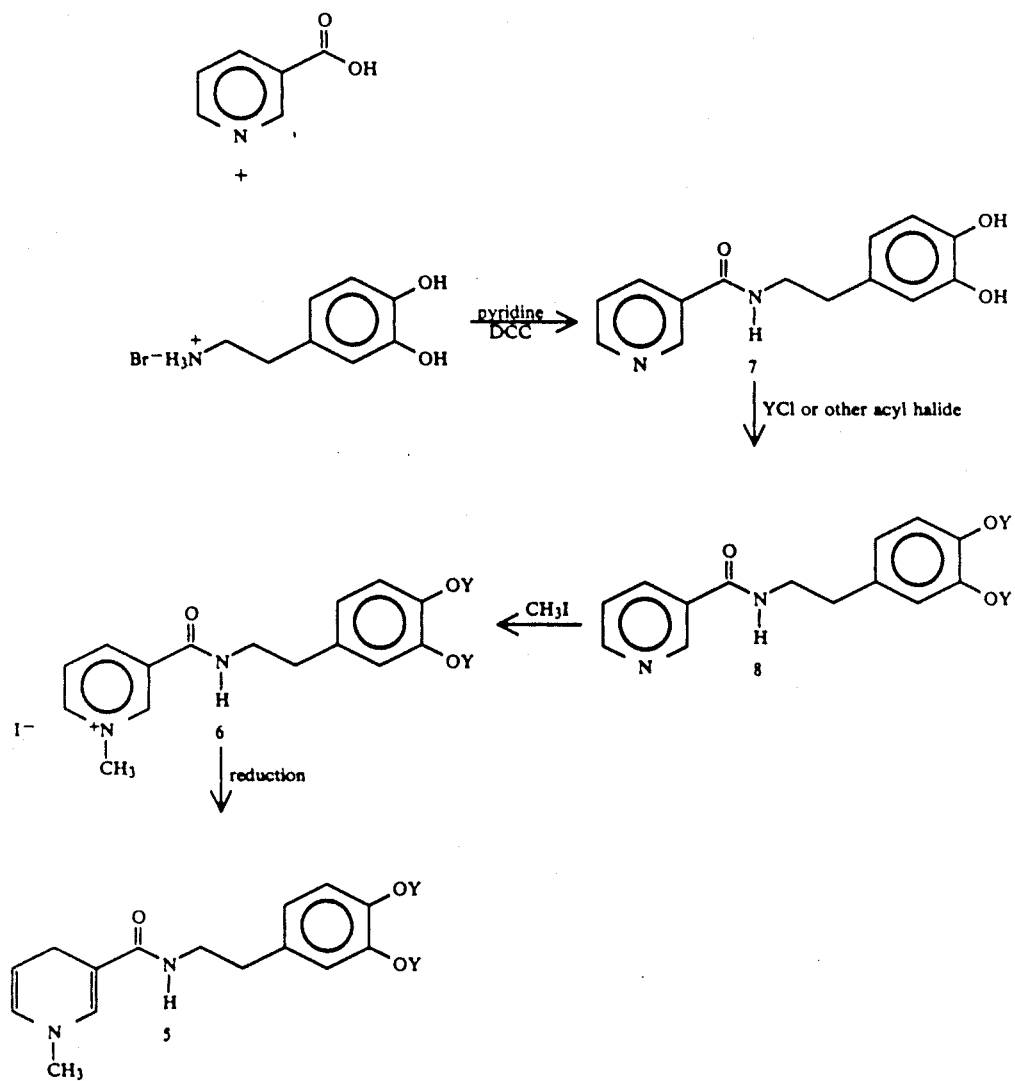
Y = COCH₃ (b) or COC(CH₃)₃ (c)
DCC = dicyclohexylcarbodiimide
Scheme 5
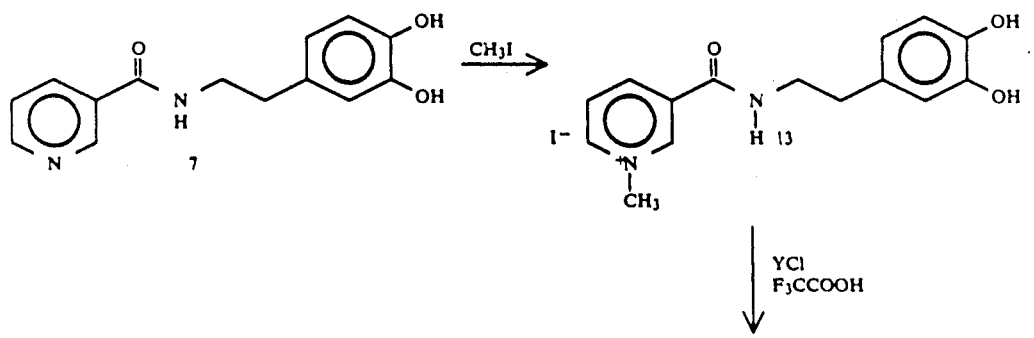

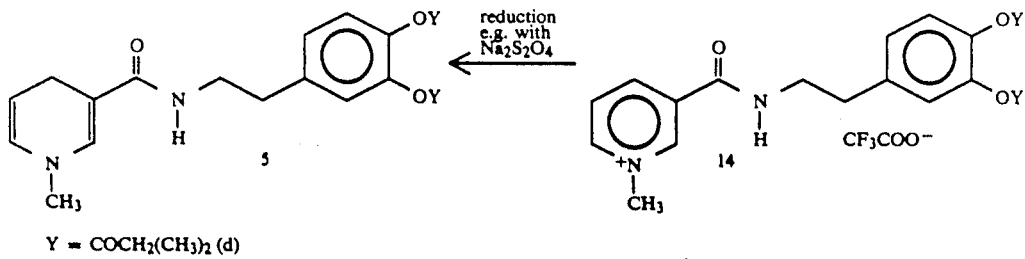

Y = COCH₂(CH₃)₂ (d)

Scheme 6

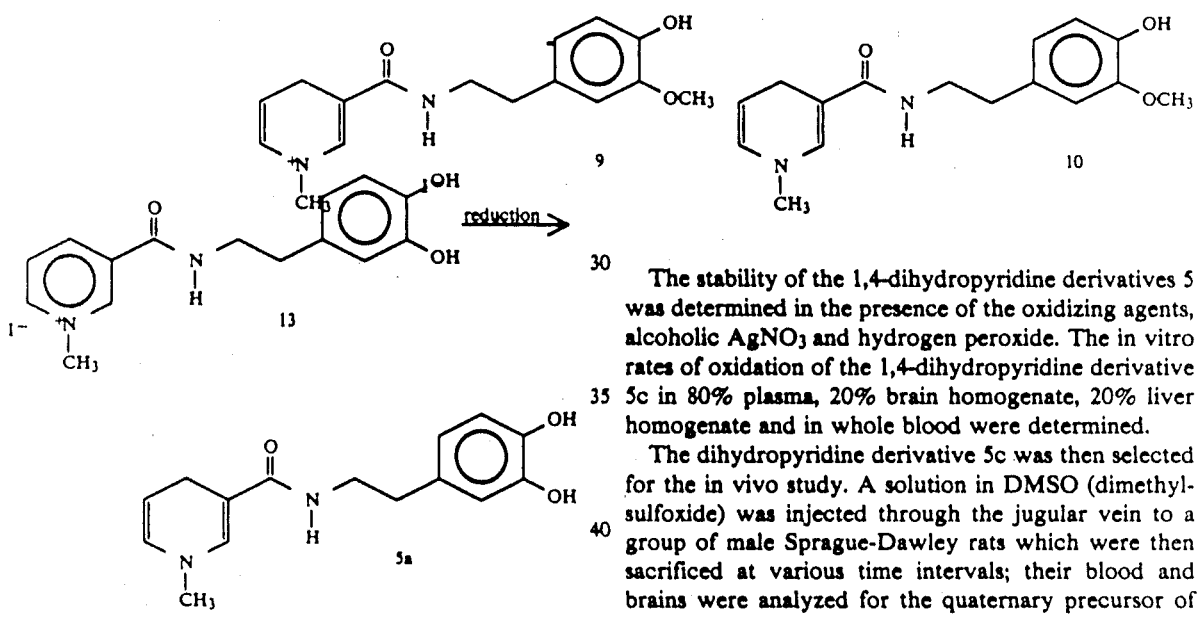

Similar schemes can be shown for the preparation of the other dopamine derivatives of the invention. The steps which introduce the protecting groups are of course only required when it is desired to protect the catechol hydroxyl groups. Moreover, when carbonate rather than acyl protecting groups are desired, the step of introducing the protecting groups will involve reacting the catechol with a halocarbonate of the type Y'O-COCl or Y'OCOBr (formed by reaction of Y'OH with COCl₂ or COBr₂), rather than with an acyl halide YCl or YBr, Y and Y' being as generically defined hereinabove. Also, the order of steps shown, e.g. in Scheme 4, may be altered; quaternization, followed by reduction, need not be the final two steps but may be carried out earlier in the reaction sequence. Yet other reaction schemes and reactants (e.g., using an anhydride rather than an acyl halide to convert 7 or 8) will be readily apparent to those skilled in the art, Schemes 4 and 5 being simply preferred approaches for the specific compounds there depicted.

In an attempt to ascertain whether any biotransformation of the free catechol is taking place by COMT (catechol-O-methyltransferase) either before or after oxidation, the possible O-methyl metabolites 9 and 10 were synthesized separately following Scheme 4 with 3-methoxytyramine hydrochloride as the starting material.

The stability of the 1,4-dihydropyridine derivatives 5 was determined in the presence of the oxidizing agents, alcoholic AgNO₃ and hydrogen peroxide. The in vitro rates of oxidation of the 1,4-dihydropyridine derivative 5c in 80% plasma, 20% brain homogenate, 20% liver homogenate and in whole blood were determined.

The dihydropyridine derivative 5c was then selected for the in vivo study. A solution in DMSO (dimethylsulfoxide) was injected through the jugular vein to a group of male Sprague-Dawley rats which were then sacrificed at various time intervals; their blood and brains were analyzed for the quaternary precursor of dopamine 6a. The in vivo dopaminergic activities of the selected compounds 5c vs. 6a were then determined.

Consistent with the above, it was found that N-nicotinoyldopamine 7 could be obtained in good yields by coupling dopamine hydrobromide with nicotinic acid in pyridine as a solvent and with dicyclohexylcarbodiimide as the coupling agent. Attempts to prepare 7 by using dopamine free base were largely unsuccessful. As for the catechol protecting groups, the acetyl and pivalyl moieties were initially selected due to their rather different steric and partitioning parameters. Acylation could be accomplished with the acyl chlorides by using conventional methods. Reduction of the quaternaries 6a-c and 9 was accomplished by using sodium dithionite in mildly basic aqueous solution (NaHCO₃). It was observed that the dihydro compound obtained in the case of the quaternary 6b gave a faint green color with ferric ions, indicating partial hydrolysis of at least one of the acetyl moieties during reduction, even in the cold, weakly basic solution used as a medium. The dihydropyridine derivatives isolated 5a-c and 10 were determined to have the expected 1,4-dihydropyridine structure, based on their NMR and UV spectra. Attempts to prepare the β-protonated enamine salts of the isolated dihydro derivatives were also largely unsuccessful, due to acid catalyzed addition reactions. The 1,4-dihydropyridine derivatives 5a–c were found to be relatively stable towards oxidation. Compound 5c was quantitatively oxidized to the corresponding quaternary salt 6c by $H_2O_2$ or alcoholic $AgNO_3$ solution.

Figure 5:
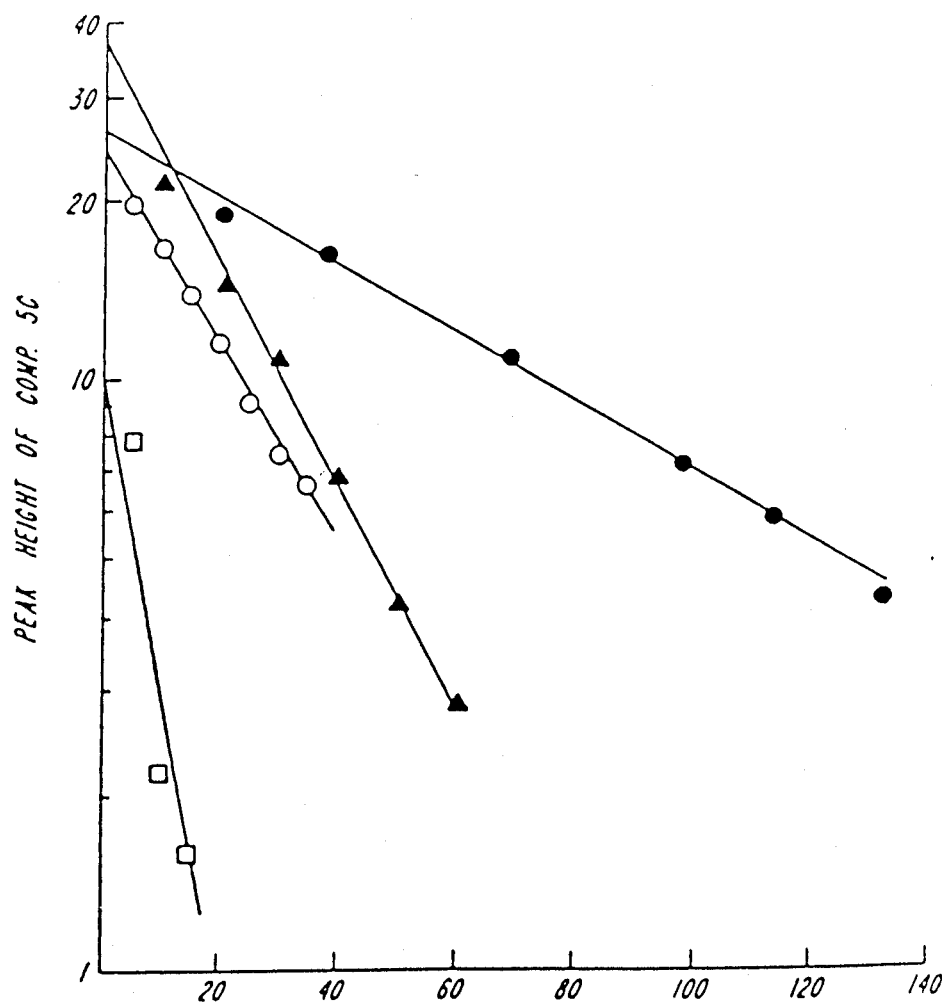
FIG. 5 is a semilog plot of peak heights of 1-methyl-3-{N-[β-(3,4-dipivalyloxyphenyl)ethyl]}-carbamoyl-1,4-dihyropyridine 5c against time in plasma (●), brain homogenate (▲), whole blood ⊖ and liver homogenate (□)

The diacetyl derivatives 5b and 6b appeared to be labile to hydrolysis and therefore were not pursued in vitro. The dipivalyldihydro derivative 5c was thoroughly investigated for its in vitro rates of disappearance and metabolic degradation in various biological fluids. It is evident that 5c represents a rather complex case, as besides oxidation, a two-step hydrolysis will also take place. Scheme 7 illustrates the interconversion of the possible components.

data fit very closely a pseudo first order process (FIG. 5). The obtained values, 51 min (80% plasma), 17 min (20% brain homogenate), 18 min (whole citrated blood) and 6 min (20% liver homogenate), reflect an acceptable stability of the dihydro derivative 5c. The disappearance of 5c is accompanied by formation of some monoester 11 and dihydroxy dihydro form 5a in all the media except the liver homogenate. The rate of hydrolysis of the first ester moiety is faster than the second and a reasonable amount of monoester 11 builds up with time. The monohydroxy quaternary 12 could not be detected except in the blood as a very small peak which does not change significantly with time. A steady increase in the concentration of the dihydroxy quaternary 6a was observed in all media except liver homogenate. Thus, it is established that this derivative, 6a, is forming

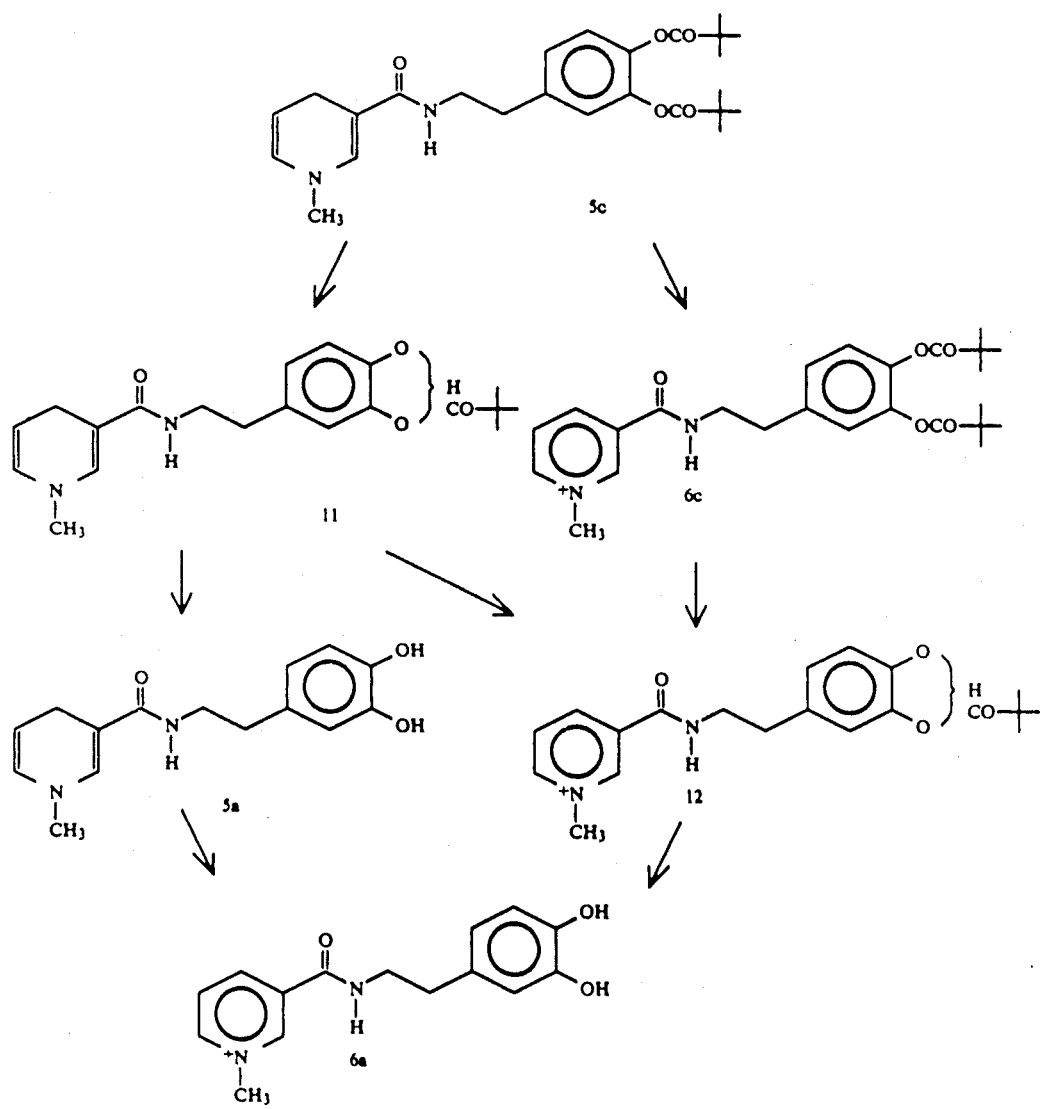

Scheme 7

FIGS. 1–4 illustrate the results of such an investigation. The apparent half-lives for the disappearance of 5c in biological fluids at 37° C. were calculated. Although the process does not truly follow first order kinetics, the as the main product of the various interconversion routes and it is the direct precursor thus concluded to be locked in the brain in the in vivo experiment. No formation of the methoxy derivatives 9 and 10 could be detected in any of the biological fluids studied; 5a and 6a do not appear to be good substrates for COMT.

Figure 6:
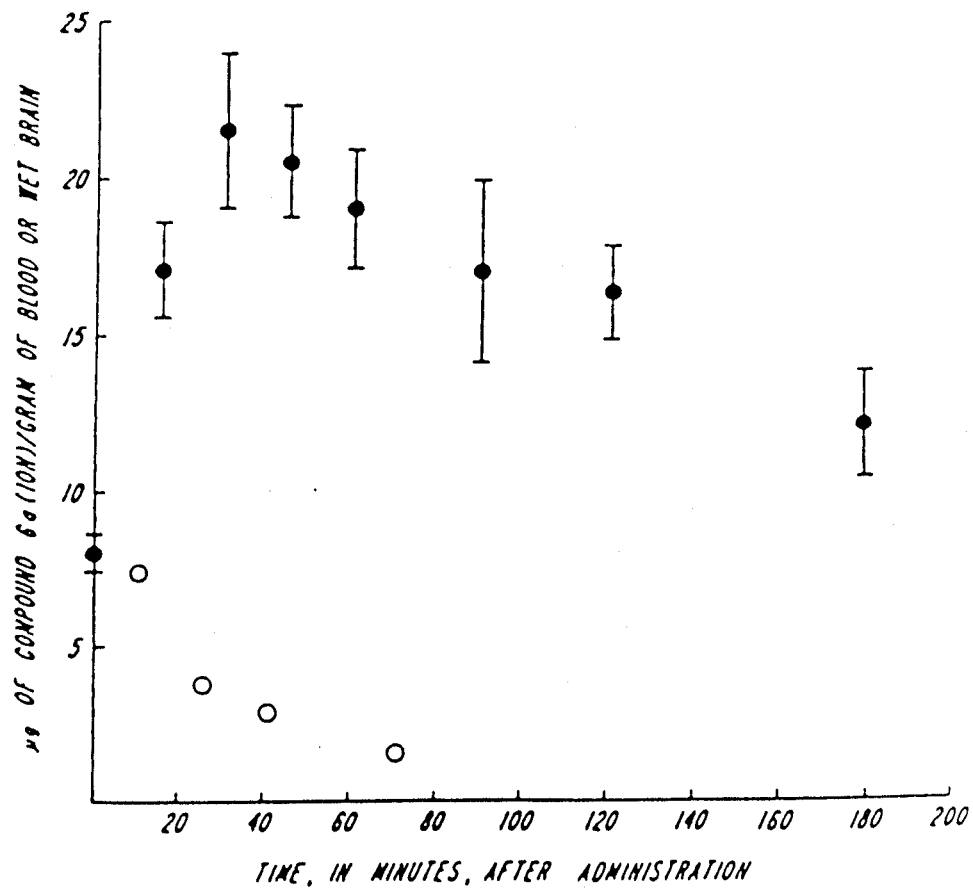
FIG. 6 is a graph plotting concentrations against time of 1-methyl-3-{N-[β-(3,4-dihydroxyphenyl)ethyl]}carbamoyl pyridinium cation 6a in brain (●) and in blood ⊖ following administration of 1-methyl-3-{N-[β-(3,4-dipivalyloxyphenyl)ethyl]}-carbamoyl-1,4-dihydropyridine 5c, with the error bars indicating SEM.

The first objective of the in vivo studies was to trace the appearance and disappearance of 6a in blood and brain following administration of 5c. FIG. 6 summarizes such results, and is consistent with the mechanism shown in Scheme 3. After one single injection of the 1,4-dihydropyridine derivative 5c to the rat, the dihydroxy quaternary 6a (ion), which is the only detectable derivative, could be seen to appear and then to disappear quickly from the blood, with a half-life of 27 min. On the contrary, the concentration of 6a (ion) is increasing in the brain steadily, reaching a maximum at about 30 min following administration. The descending portion indicates a half-life of disappearance from the brain of about 3.2 h. No formation of O-methyl metabolites 9 and 10 could be detected in the brain. This confirms the in vitro results that 6a (or 5a) is not a good substrate for COMT.

Figure 7:
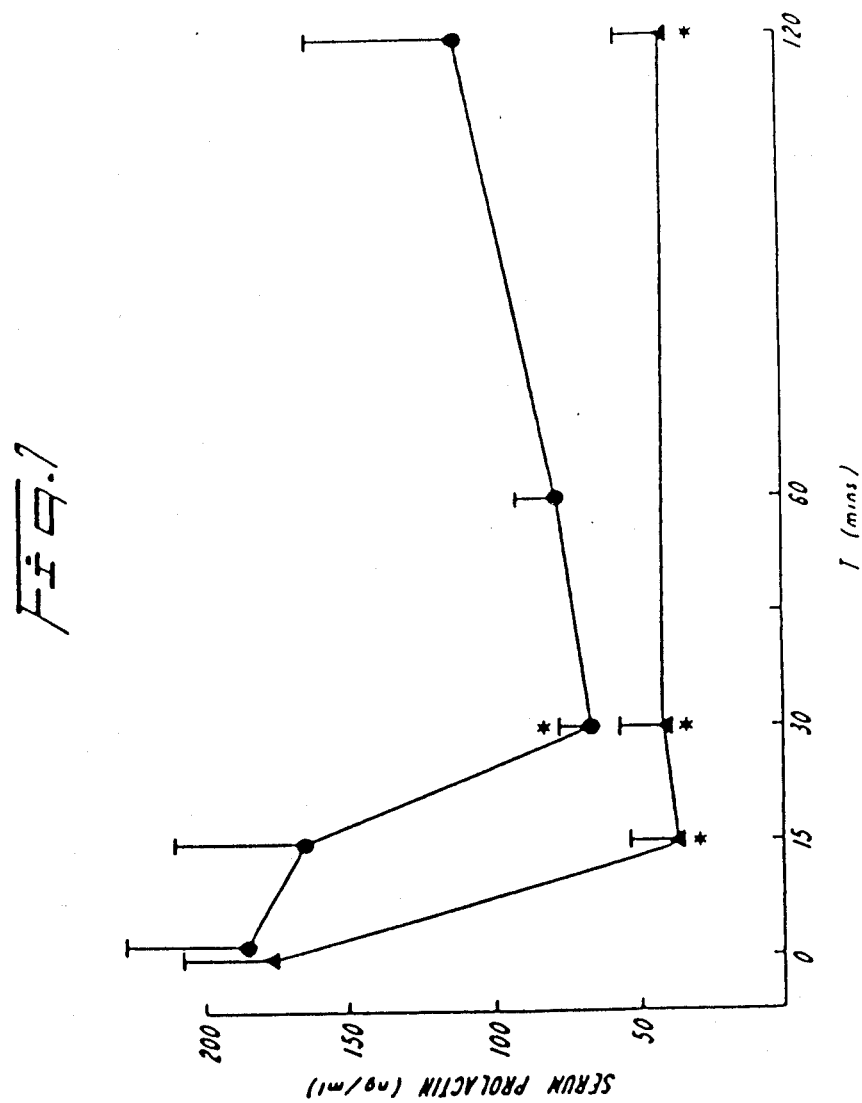
FIG. 7 is a graph plotting the effects of compounds 5c (▲) and 6a (●) administered I.V. at a 1 mg/kg dose level, on the serum prolactin levels in rats.

To determine whether dopamine itself was finally released in the brain upon completion of the aforesaid complex delivery process, 5c was administered intrajugularly and changes in brain-dopamine concentrations by 15 min, and caused a 67% reduction by 30 min. Thereafter, serum prolactin levels increased progressively to levels which are not significantly different from vehicle injected controls, by 60 and 120 min. These results are summarized in FIG. 7. The rapid onset and prolonged inhibitory effects of 5c on prolactin secretion is consistent with the time course of the appearance of 6a in the brain following administration of 5c. The "trapping" of 6a in the brain subsequent to I.V. injection of 5c provides a constant source of a potent dopaminergic agent, either dopamine or 6a itself. The significantly lower effect of 6a when administered I.V. does not unequivocally clarify which alternative is the more responsible. This was resolved by in vitro comparison of the relative activities of dopamine versus 6a.

Fresh anterior pituitaries obtained from female rats were incubated with various concentrations of dopamine (DA) and 6a, respectively, and their effects on the rate of release of prolactin were measured. It was found that at $2\times10^{-8}$M concentrations, neither DA nor 6a had any effect, but at $2\times10^{-7}$M, DA caused a 57% reduction of the prolactin rate secretion, while 6a had no effect. These results are summarized in the following Table I.

TABLE I

Comparative in vitro activity of 6a vs. dopamine[a]
Prolactin ng/mg./h[b]

| Dopamine (DA)[c] | | | | 6a[d] | | | |
|---|---|---|---|---|---|---|---|
| Control | DA $2\times10^{-8}$M | Control | DA $2\times10^{-7}$M | Control | 6a $2\times10^{-8}$M | Control | 6a $2\times10^{-7}$M |
| 344 ± 50 | 355 ± 67 | 282 ± 34 | 121 ± 38* | 342 ± 38 | 386 ± 29 | 250 ± 30 | 277 ± 32 |

[a]On freshly obtained anterior pituitary (AP) at 37° C. All values are average of 9 separate AP-S.
[b]Prolactin release rate of the incubated AP-S.
[c]Weight of the AP-S: Control 4.6 ± 0.2 mg. DA treated 4.5 ± 0.3 mg.
[d]Weight of the AP-S: Control 4.6 ± 0.3 mg. 6a treated 4.7 ± 0.4 mg.
*$P < 0.05$ tions following that administration were studied. Some of the rats showed up to threshold increase in the dopamine concentrations, others practically none. Since it is possible (and even desired) that the intrinsic brain metabolism of the dopamine does not permit significant build-up of its concentration, specific pharmacologic activity was investigated, using changes in the in vivo prolactin secretion. It is known that dopamine and its agonists decrease prolactin secretion following their binding to stereospecific receptors located on lactophors in the anterior pituitary (AP) gland [G. P. Mueller, J. W. Simpkins, J. Meites and K. E. Moore, Neuroendocrinology, 20, 121 (1976); W. Wuttke, E. Cassell and J. Meites, Endocrinology, 88, 737 (1971); J. A. Clemens, E. B. Smalstig and C. J. Shaar, Acta Endocrinol., 79, 230 (1975)]. This effect is dose-dependent and it can also be observed in vitro, incubating anterior pituitaries with dopamine or its agonists [R. M. MacLeod in "Frontiers in Neuroendocrinology", Ed. L. Martini and W. F. Ganong, Raven Press].

It was then determined that exposure of male rats to 17β-estradiol for two days elevated serum prolactin levels to greater than 150 ng/ml. Intravenous administration of 5c caused a 79% decrease in serum prolactin concentrations and this dramatic reduction was maintained through 120 min after treatment. In contrast, 6a had no significant effect on the serum prolactin concen- These results indicate that if 6a has any activity, it must be significantly less than that of DA. Based on the delayed onset of the activity when 6a was administered I.V. and considering the in vitro results, it logically follows that the high and prolonged activity of the 6a locked in the brain following administration of 5c is due to the fact that 6a is slowly releasing the active DA in the brain.

Further studies provided direct evidence that a redox dopamine delivery system increases brain levels of dopamine and data which suggests that the dopamine formed is delivered to sites normally occupied by newly synthesized dopamine (DA). The chemical delivery systems for DA evaluated in these studies are shown in Scheme 8 below. The brain-specific delivery of DA requires the oxidation of the dihydropyridine ring to the corresponding pyridinium salt 6c, 6d, hydrolysis of the pivalyl or isobutyryl esters (to 6a) and the release of DA from the "locked in" 6a.

SCHEME 8

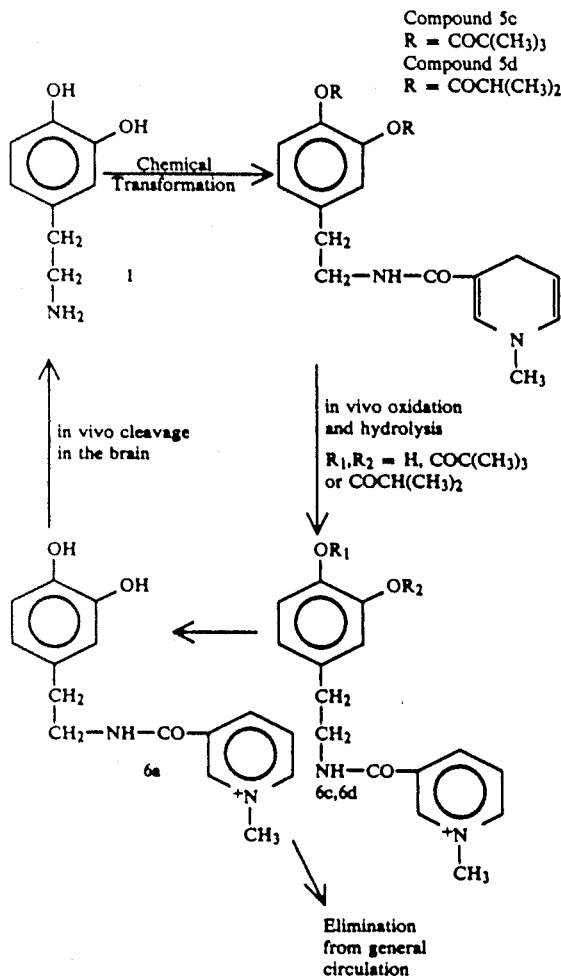

In Scheme 8, compounds 5c and 5d are the chemical delivery systems tested and 6a is the ionized dopamine precursor which accumulates in the brain, but is quickly eliminated from the rest of the body. Structures 6c, 6d depict the intermediates formed during the sequential hydrolysis and oxidation processes.

To document brain DA delivery, compound 5c was administered intravenously to male rats and the concentration of DA, dihydroxyphenylacetic acid (DOPAC) and homovanillic acid (HVA) was determined in several brain regions. After administration of 5c, concentrations of DA were unchanged, but DOPAC levels were increased by 187% in the hypothalamus, 69% in the striatum, and 374% in the cortex. HVA levels were increased in the hypothalamus, decreased in the striatum and unchanged in the cortex. (In animals treated with 5c, concentrations of norepinephrine, normetanephrine, serotonin and 5-hydroxyindoleacetic acid were not changed in any brain region examined.) Since the amount of DOPAC formed from 5c in each brain region was related to basal DA and DOPAC levels, it was concluded that the processing of 5c to DOPAC occurs primarily in dopaminergic neurons.

To evaluate the role of MAO in the processing of 5c by the brain, MAO activity was blocked with pargyline, then 5c was administered. [Lin et al, Life Sci. 8, 1077 (1969); pargyline (or saline vehicle) was administered i.p. (100 mg/kg) 1 hour prior to administration of compound 5c (50 mg/kg, i.v.) or the DMSO vehicle. Animals (6 per group) were killed by decapitation 1 hour later and tissue was processed for HPLC separation and amperometric quantitation of DA, DOPAC and HVA.] As observed before, 5c, when administered alone, increased DOPAC, but not DA, concentrations in each region evaluated. [DOPAC concentrations were increased at 1 hour after administration of compound 5c by 254% in the hypothalamus, 95% in the striatum and 177% in the cortex. As observed before (FIG. 9), HVA concentrations were increased by 35% in the hypothalamus, decreased by 67% in the striatum and not changed in the cortex.] Additionally, as expected, pargyline increased DA concentrations and reduced levels of DOPAC and HVA, indicating blockade of MAO activity. (In addition to these changes after MAO inhibition with pargyline, serotonin and norepinephrine concentrations were elevated and 5-hydroxyindoleacetic acid levels were reduced.) However, when 5c was administered to MAO-blocked rats, no elevation in DA concentrations above levels in animals treated with pargyline alone was observed. It would appear that MAO action on the mono- or dipivalyl esters of DA is not a likely explanation for the inability to demonstrate DA formation from the chemical delivery system. Presumably, even with MAO blockade, the formed DA can be metabolized by other enzymatic pathways. Chiba et al, Biochem. Biophysic Res. Comm. 120, 574 (1980) demonstrated that MAO catalyzed the oxidation of a tetrahydropyridine. Thus, it is possible that MAO oxidizes compounds 5c and 5d (both dihydropyridines) to compound 6c or 6d, in which case formation of DA from the delivery system would be blocked by pargyline.

Figure 8:
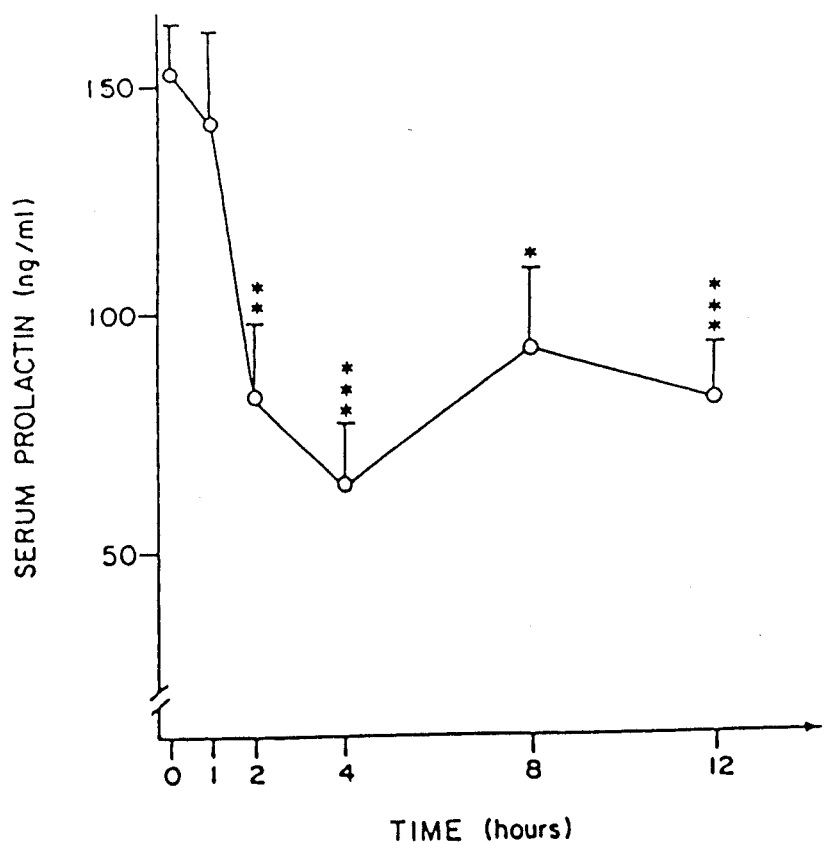
FIG. 8 is a graph plotting the effect of compounds 5c ⊖ administered I.V. at a 1 mg/kg dose level on serum prolactin concentration in rats over an extended period of time.

Serum prolactin concentrations were measured and behavioral stereotypy was monitored in rats treated with 5c to test for effective brain specific dopaminergic activity even in the absence of increased DA concentrations. Since 6c/6d is without prolactin inhibiting activity at concentrations as high as $10^{-5}M$ in an in vitro anterior pituitary preparation [Bodor et al, Science 221, 65 (1983); DA at $10^{-6}$ and $10^{31}$ $^5$N reduced pituitary prolactin release by 71 and 85%, respectively, but 6a was without effect on prolactin release at either dose], sustained suppression of serum prolactin would be due to the formation of DA from 5c in the hypothalamus. Intraveneous injection of 5c reduced serum prolactin levels by 40 to 59% from 2 to 12 hours and levels of the hormone normalized by 24 h (FIG. 8). However, stereotypic activity was not detected at any of these times in response to the drug. Thus, DA may be selectively formed and released in the hypothalamus at a rate which suppresses pituitary prolactin release but does not induce stereotypy. This is not surprising since prolactin inhibition is detected at doses of dopaminergic drugs which are 10 to 30 times lower than that needed to induce stereotypic behavior [Annunziato et al, Eur.

J. Pharmacol. 50, 187 (1978); Mueller et al, Neuroendocrinol. 20, 121 (1976)].

Figure 10:
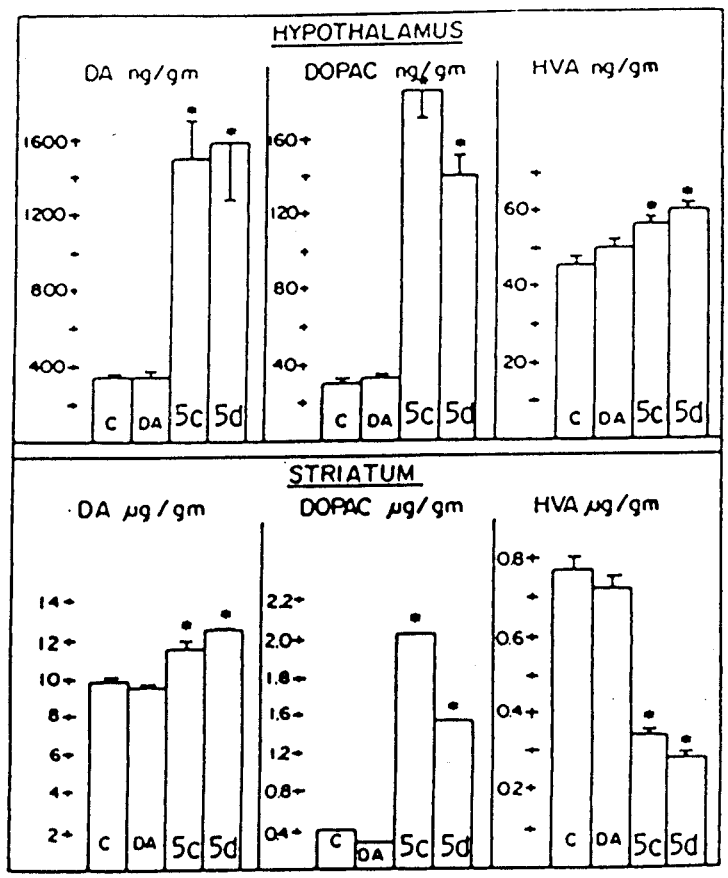
FIG. 10 consists of bar graphs showing the effects of blockade of endogenous dopamine synthesis on concentrations of dopamine (DA), dihydroxyphenylacetic acid (DOPAC) and homovanillic acid (HVA) in specific brain regions after administration of dopamine (DA), 1-methyl-3-{N-[β-(3,4-dipivalyloxyphenyl)ethyl]}carbamoyl-1,4-dihydropyridine (5c) and 1-methyl-3-{N-[β-(3,4-diisobutyryloxyphenyl)ethyl]}carbamoyl-1,4-dihydropyridine (5d).

To document DA formation from the delivery system, animals were treated with 5c, 5d or DA itself, intravenously, and 30 minutes later the aromatic amino acid decarboxylase inhibitor, m-hydroxybenzylhydrazine (NSD 1015), was administered to block formation of endogenous DA [Carlsson, in Pre- and Post-Synaptic Receptors, eds. E. Usdin and W. E. Bunney, Marcel Dekker Press, pp. 49–63 (1975)]. While DA administration did not alter concentration of DA, DOPAC or HVA in the striatum or hypothalamus, 5c and 5d caused a 17 to 20% increase in striatal DA levels and a 4.5-fold increase in hypothalamic DA levels (FIG. 10). As expected, DOPAC concentrations were increased in both the striatum and hypothalamus after 5c or 5d, and HVA levels were increased in the hypothalamus but decreased in the striatum. These data demonstrate that inhibition of endogenous DA synthesis is required to document DA delivery by our redox system and suggest that DA formed from 5c and 5d compete with newly synthesized DA for available storage vesicles. Since newly synthesized DA is preferentially released from dopaminergic neurons [Kopin et al, J. Pharmacol. Exp. Ther. 161, 271 (1968); Weiner et al, in New Concepts in Neurotransmitter Regulation, Plenum Press, New York, 1973, pp. 89–113], the DA formed from 5c or 5d would appear to replete a functional, releasable pool of DA.

The redox DA delivery system exerted differential metabolic and pharmacologic effects in the hypothalamus and striatum. In normal rats, the delivery system reduced serum prolactin in association with increased hypothalamic concentrations of both DOPAC and HVA, while in the striatum, the increase in DOPAC levels was consistently associated with a reduction in HVA concentrations and an absence of stereotypy. HVA is formed by the sequential 3-O-methylation of DA by catecholamine-O-methyl transferase (COMT) and the deamination by MAO of the resulting 3-O-methyltyramine [Azelrod et al, J. Biol. Chem., 233, 702 (1958); Jonason, Acta Physiol. Scand. 76, 229 (1969)]. The increase in hypothalamic HVA following 5c or 5d may indicate enhanced DA release since, among other neuronal sites, COMT is located on the post-synaptic membranes. This interpretation is consistent with the reduction in serum prolactin associated with in vivo administration of 5c, and evidence for the relative absence of autoreceptors for DA or an effective DA reuptake system in tuberinfundibular neurons [Snyder er al, J. Pharmacol. Exp. Ther 165, 78 (1969)]. Thus, in the hypothalamus and in particular the tuboinfundibular DA system, DA is formed from this chemical delivery system, and appears to be released from nerve terminals and delivered to the pituitary to inhibit prolactin secretion.

While DA is formed from 5c or 5d in the striatum, stereotypy was not observed and reduced HVA concentrations were consistently found. Collectively, these observations indicate that concentrations of striatal DA achieved by the drug are not sufficient to cause the profound stimulation of striatal DA receptors needed to induce stereotypy (Annuziato et al, supra; Mueller et al, supra).

The observed regional difference in DA concentrations in response to 5c or 5d likely reflect the nerve terminal composition of the striatum and the hypothalamus. The monoaminergic terminals in the striatum are predominantly dopaminergic [Fuxe, Acta Physiol. Scan. 64, Suppl. 247, 37 (1965); Moore et al, Ann. Rev. Neurosci. 1, 129 (1978); Moore et al, Ann. Rev. Neurosci. 2, 113] and here the aromatic amino acid decarboxylase inhibitor, NSD 1015, selectively reduced de novo DA synthesis. Thus, the DA formed from 5c or 5d would be expected to occupy DA storage sites almost exclusively and we observed a modest increase in striatal DA following administration of the redox delivery system. In contrast, the monoaminergic nerve terminals in the hypothalamus are heterogeneous (Fuxe et al, supra; Moore et al, supra) and NDS 1015 reduces the synthesis of serotonin and norepinephrine as well as DA [Ng et al, Science 172, 487 (1971); Snyder et al, J. Pharmacol. Exp. Ther. 165, 78 (1968); Karobath et al, J. Pharmacol. 14, 393 (1971)]. The DA formed from 5c or 5d could occupy vesicular space in all three types of neurons [Glowinski et al, Neurochem. 13, 655 (1966)] and this may account for the 4.5-fold increase in hypothalamic DA concentrations after administration of 5c or 5d.

Thus, it has been demonstrated that a chemical DA delivery system as described herein selectively reduces prolactin secretion in animals with normal dopaminergic neuronal activity and increases DA concentrations in the striatum and hypothalamus in animals with reduced DA synthesis. This DA delivery system is expected to be useful in the selective treatment of hyperprolactinemia as well as in the treatment of DA deficiencies in other brain regions. This method of brain delivery of DA is expected to be useful particularly to evaluate for and treat dopaminergic deficiencies caused by a decline in endogenous DA synthesis.

The representative dopamine delivery systems tested appear to preferentially affect the hypothalamus and the functions which it regulates, i.e. prolactin secretion. Dopaminergic drugs with selectivity for hypothalamic dopaminergic systems have an obvious advantage in the treatment of hyperprolactinemia. Moreover, the apparently unique mechanism of action of these dopamine delivery systems, i.e. vesicular repletion, may make these compounds particularly useful for long-term therapy. That is, because only the dopamine which can be stored is pharmacologically active, longterm toxicity of the dopamine delivery system should be minimal. This latter characteristic could provide a particular advantage over the currently used bromocriptine. The need for long-term dopamine therapy has recently become evident from observations that hyperprolactinemia frequently reappears in patients who had "successful" tumors removed years earlier [Serri et al, N. Eng. J. Med. 309, 280–283 (1983)]. In these patients, life-long therapy with bromocriptine would be required and the resulting potential for associated toxicity of the drug is evident.

Accordingly, provided hereby is a potent, brain-specific dopaminergic agent comprising a lipophilic dihydropyridine carrier-type chemical delivery system of dopamine ["pro-prodrug" or "pro-pro-prodrug" in the case of the catechol protective group(s)], which penetrates the BBB by passive transport. The rapid oxidation in the brain of the carrier moiety to the corresponding quaternary pyridinium salt results in an activated amide of dopamine. The oxidation process is much faster than amide cleavage of the beginning compound 5 or of 6. Moreover, the ionic nature of the activated quaternary salt results in a significant slowdown of the efflux of this specific form through the BBB, resulting in a selective concentration enhancement of the precursor 6a in the brain. Too, brain-specific dopaminergic activity is assured, logically as dopamine is released from this activated form upon hydrolytic, enzymatic or metabolic cleavage, as is facile excretion of the carrier moiety from the brain.

And as disclosed in my parent applications Ser. Nos. 461,543, 516,382 and 665,940, as well as in their parent Ser. No. 379,316 (now U.S. Pat. No. 4,479,932), it will again be appreciated that by "dihydropyridine carrier" or "[DHC]", there is intended any nontoxic carrier moiety comprising, containing or including the dihydropyridine nucleus, whether or not a part of any larger basic nucleus, and whether substituted or unsubstituted, the only criterion therefor being capacity for both BBB-penetration and in vivo oxidation thereof to the corresponding quaternary pyridinium salt carrier [QC]+. As aforesaid, the ionic pyridinium salt dopamine/carrier prodrug entity [D-QC]+ which results from such in vivo oxidation is prevented from efflux from the brain, while elimination from the general circulation is accelerated. Subsequently, the covalent or equivalent bond coupling the dopamine species [D] to the quaternary carrier [QC]+ is likely metabolically cleaved which results in sustained delivery of the dopamine [D] in the brain and facile elimination of the carrier moiety [QC]+. Such "covalent or equivalent bond" between the dopamine and the quaternary carrier can be a simple direct chemical bond, e.g., an amide, or any other like bond, or same can even be comprised of a linking group or function. Nonetheless, the bond in the formulas [D-QC]+ and [D-DHC] is intended to be, and is hereby defined as, inclusive of all such alternatives. An the cleavage of the [D-QC]+ prodrug to sustainedly deliver the drug species [D] in the brain with concomitant facile elimination of the carrier moiety [QC]+ is characteristically enzymatic cleaage, e.g., by amidase, albeit any type of in brain cleavage which might result, whether enzymatic, metabolic or otherwise, of course remains within the ambit of this invention. Thus, the drug release rate controlling parameter of the subject pro-pro-drugs is imparted simply via the cleavable bonding between dopamine and carrier. Lastly, the illustrations of suitable redox carriers and "bonds" disclosed in my said copending applications and in their parents are hereby specifically incorporated by reference. In particular, dihydropyridine⇌pyridinium salt redox carrier moieties for use herein include the following quaternaries [QC]+ corresponding dihydro forms:

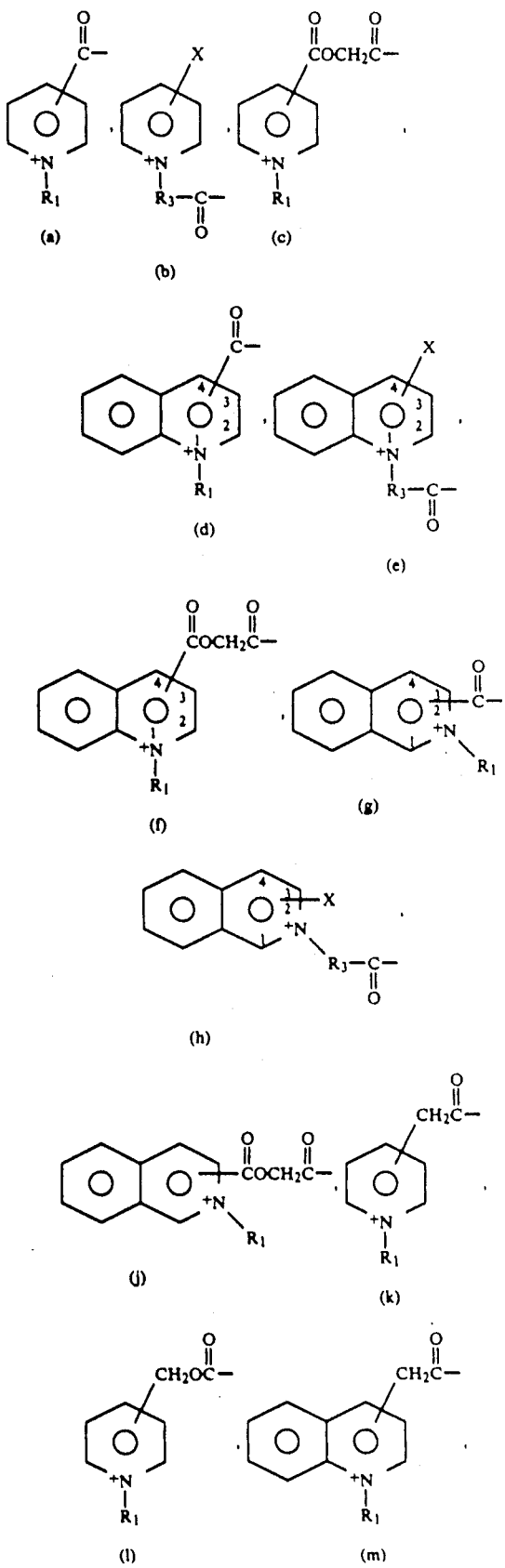

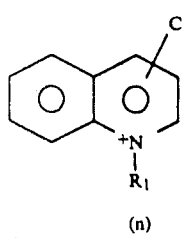

(n)

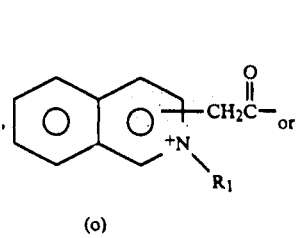

(o)

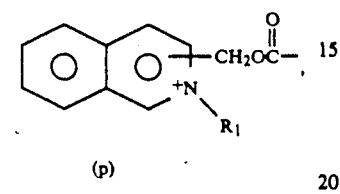

(p)

wherein $R_1$ is $C_1$–$C_7$ alkyl, $C_1$–$C_7$ haloalkyl or $C_7$–$C_{10}$ aralkyl; $R_3$ is $C_1$ to $C_3$ alkylene; X is —CONR'R" wherein R' and R", which can be the same or different, are each H or $C_1$–$C_7$ alkyl, or X is —CH=NOR"' wherein R"' is H or $C_1$–$C_7$ alkyl; the carbonyl-containing groupings in formulas (a), (c), (k) and (l) and the X substituent in formula (b) can each be attached at the 2, 3 or 4 position of the pyridinium ring; the carbonyl-containing groupings in formulas (d), (f), (m) and (n) and the X substituent in formula (e) can each be attached at the 2, 3 or 4 position of the quinolinium ring; and the carbonyl-containing groupings in formulas (g), (j), (o) and (p) and the X substituent in formula (h) can each be attached at the 1, 3 or 4 position of the isoquinolinium ring.

The dihydro forms [DHC] corresponding to the aforementioned quaternaries are as follows:

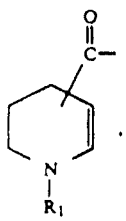

(a')

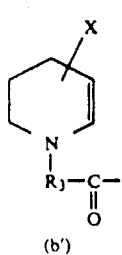

(b')

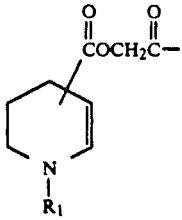

(c')

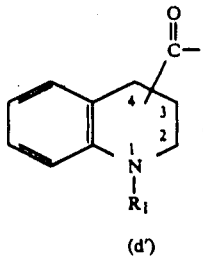

(d')

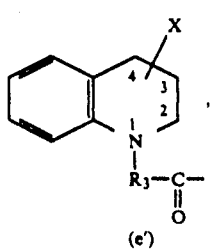

(e')

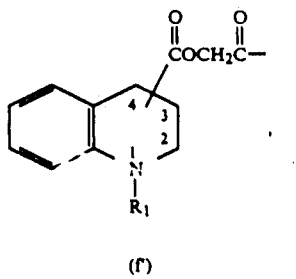

(f')

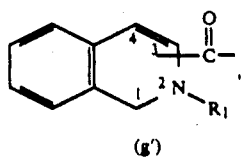

(g')

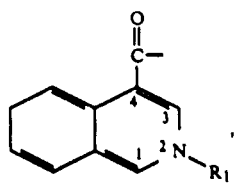

(g")

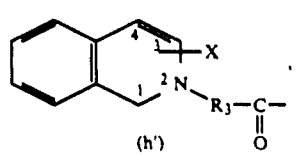

(h')

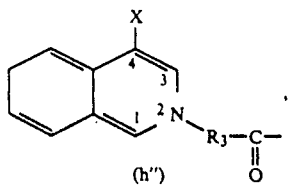

(h")

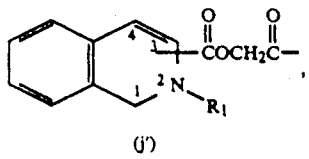

(j')

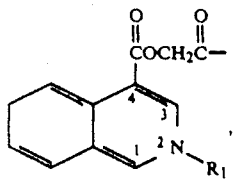

(j")

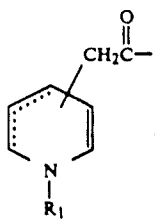

(k')

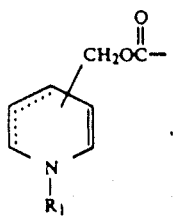

(l')

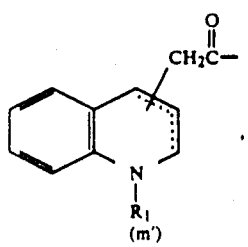

(m')

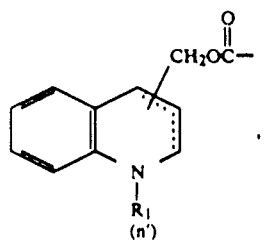

(n')

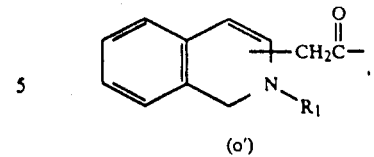

(o')

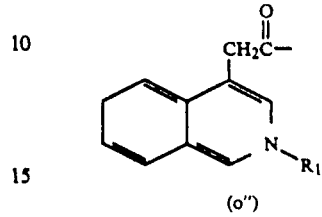

(o")

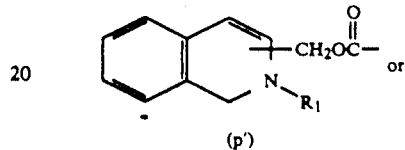

(p')

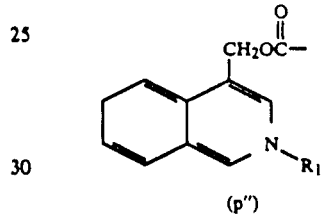

(p")

wherein the dotted line in formulas (a'), (b'), (c'), (k') and (l') indicates the presence of a double bond in either the 4 or 5 position of the dihydropyridine ring; the dotted line in formulas (d'), (e'), (f'), (m') and (n') indicates the presence of a double bond in either the 2 or 3 position of the dihydroquinoline ring; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R", wherein R' and R", which can be the same or different, are each H or $C_1$-$C_7$ alkyl, or X is —CH=NOR'" wherein R'" is H or $C_1$-$C_7$ alkyl; the carbonyl-containing groupings in formulas (a'), (c'), (k') and (l') and the X substituent in formula (b') can each be attached at the 2, 3 or 4 position of the dihydropyridine ring; the carbonyl-containing groupings in formulas (d'), (f'), (m') and (n') and the X substituent in formula (e') can each be attached at the 2, 3 or 4 position of the dihydroquinoline ring; and the carbonyl-containing groupings in formulas (g'), (j'), (o') and (p') and the X substituent in formula (h') can each be attached at the 1, 3 or 4 position of the dihydroisoquinoline ring.

The carrier moieties set forth above are intended for linkage to the amino function of dopamine, replacing a hydrogen atom of said function with one of the depicted [QC]+ or [DHC] groups. The groups illustrated are merely exemplary, not exhaustive, of the many classes of carriers contemplated by this invention.

Here and throughout this application, the expression "$C_1$-$C_7$ haloalkyl" means $C_1$-$C_7$ substituted by one or more halogen atoms. Also here and throughout this application, the alkyl radicals, including alkyl and alkylene portions of other radicals, can be straight or branched unless otherwise specified.

The presently preferred dihydropyridine⇌pyridinium salt redox carrier moieties of this invention are those wherein $R_1$, when present, is —$CH_3$; $R_3$, when present, is —$CH_2CH_2$—; X when present, is —$CONH_2$; the depicted carbonyl-containing groupings in formulas (a), (c), (k) and (l) and the X substituent in formula (b) are attached at the 3-position; the depicted carbonyl-containing groupings in formulas (d), (f), (m) and (n) and the X substituent in formula (e) are attached at the 3-position; the depicted carbonyl-containing groupings in formulas (g), (j), (o) and (p) and the X substituent in formula (h) are attached at the 4-position; and the corresponding dihydro moieties.

Especially prefered dihydropyridine⇌pyridinium salt redox carrier moieties are the quaternaries of structures (a), (b), (d), (e), (g) and (h); and the corresponding dihydro forms, most especially when they contain the preferred structural variables identified in the preceding paragraph.

In one embodiment according to this invention, simple nontoxic carrier systems [D-QC]$^+$⇌[D-DHC] are envisaged for dopamine. A representative such carrier system is:

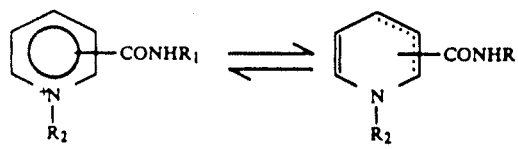

wherein

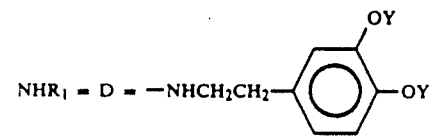

wherein Y is defined as before (i.e. a dopamine residue) and $R_2$ is simply alkyl, e.g., $CH_3$, or benzyl, albeit virtually any other effective substituent is intended. (As depicted above, the isomeric dihydropyridine structure depends on the position of the substituent relative to the pyridine nitrogen.) Exemplary of such simple carrier systems are N-alkyl nicotinamide derivatives, tethered to dopamine. The trigonelline (N-methylnicotinic acid) system is quite effective as a carrier; it also is readily eliminated from the circulation and is virtually nontoxic.

Indeed, the present invention provides a flexible arsenal of dihydropyridine⇌pyridinium salt redox carriers for the site-specific/sustained delivery of dopamine to the brain. Moreover, any dihydropyridine/pyridinium salt redox carrier entity is contemplated and intended hereby generically, and any such carrier moiety need not be, and is not, derivatized with a drug release rate controlling substituent critically tailored to meet, or be coordinated with, the chemical nature and delivery requirements of the drug species sought to be preferentially administered to the brain. As utilized herein, the term "carrier" is to be understood as connoting just such a non-derivatized, non-drug/carrier coordinated entity, for consistent herewith it is the "carrier" entity itself and not the nature of any activity or release rate controlling/modifying substituent which is responsible for providing the desired brain-specific result.

Particularly preferred compounds of this invention include the following quaternaries and their corresponding dihydro forms, D in each instance representing the dopamine residue,

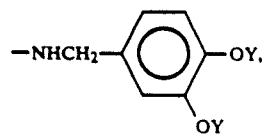

wherein each Y is independently hydrogen or a hydroxyl protecting group as defined hereinabove:

(a) the pyridinium systems

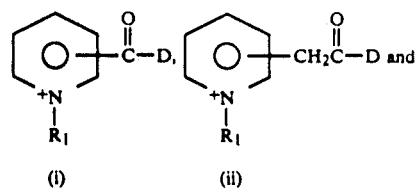

(i)   (ii)

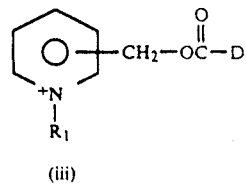

(iii)

in which the depicted substituent is in the 2, 3 or 4 position, and $R_1$ is $C_1$-$C_7$ alkyl, $C_1$-$C_7$ haloalkyl or $C_7$-$C_{10}$ aralkyl, preferably methyl or benzyl;

(b) the pyridinium system

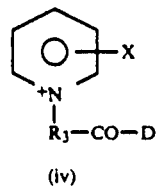

(iv)

in which X, which can be in the 2, 3 or 4 position, is —CONR'R" wherein R' and R", which can be the same or different, are each H or $C_1$-$C_7$ alkyl, or X is —CHNOR'" wherein R'" is H or $C_1$-$C_7$ alkyl, and $R_3$ is $C_1$ to $C_3$ alkylene, e.g. $(CH_2)_n$ wherein n = 1–3;

(c) the isoquinolinium and quinolinium systems

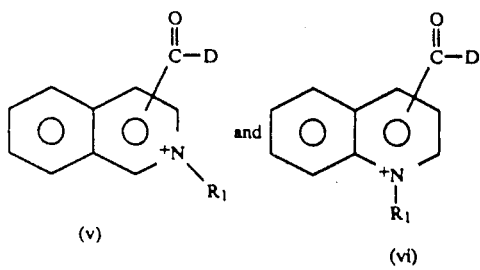

in which the depicted substituent is in the 2, 3 or 4 position of the quinolinium ring system and in the 1, 3 or 4 position of the isoquinolinium ring system and $R_1$ is defined as above; and (d) the quinolinium and isoquinolinium systems

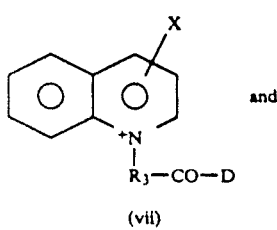

in which $R_3$ and X are defined as above, and X can be in the 2, 3 or 4 position of the quinolinium ring system and in the 1, 3 or 4 position of the isoquinolinium ring system. The corresponding dihydro forms of the foregoing preferred pyridinium salts are depicted below, wherein the position and identity of the structural variables are as indicated above.

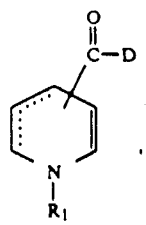

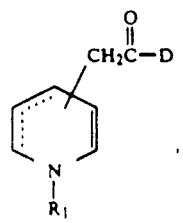

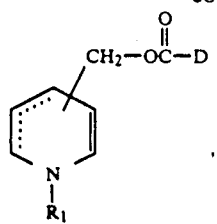

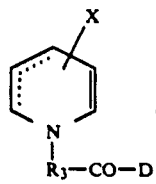

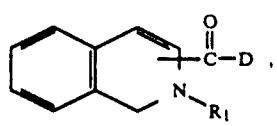

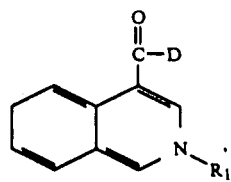

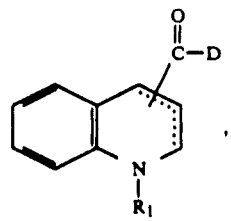

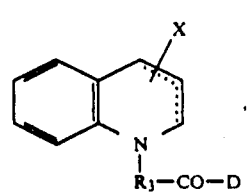

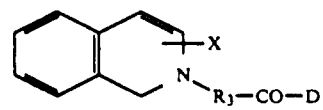

and

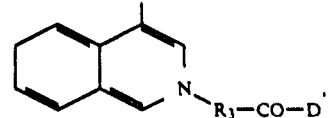

wherein the dotted lines in formulas (i'), (ii'), (iii') and (iv') indicate the presence of a double bond in either the 4 or 5 position of the dihydropyridine ring, and the dotted lines in formulas (vi') and (vii') indicate the presence of a double bond in either the 2 or 3 position of the dihydroquinoline ring.

Among the compounds of formulas (i) through (viii) and (i') through (viii''') above, those encompassed by the structures on pages 33-35 of my parent Ser. No. 461,543 are of particular interest. One particularly preferred group of compounds provided by this invention comprises compounds of the formula

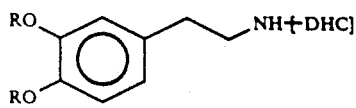 (Ia)

and the non-toxic pharmaceutically aceptable salts thereof, wherein each R is independently hydrogen or an acyl radical selected from the group consisting of alkanoyl having 2 to 8 carbon atoms;

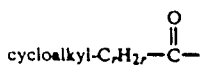

wherein the cycoalkyl portion contains 3 to 7 ring atoms and r is zero, one, two or three; and

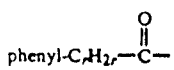

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms; and [DHC] is

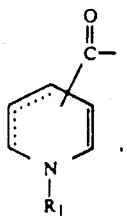 (a')

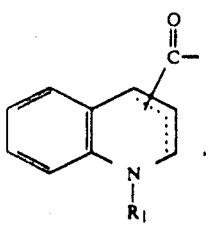 (d')

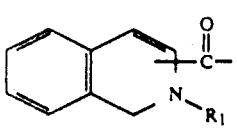 (g')

or

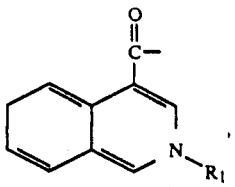 (g'')

wherein the dotted line in formula (a') indicates the presence of a double bond in either the 4 or 5 position of the dihydropyridine ring; the dotted line in formula (d') indicates the presence of a double bond in either the 2 or 3 position of the dihydroquinoline ring system;

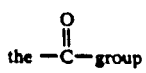

in formula (a') can be in the 2, 3 or 4 position of the dihydropyridine ring;

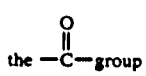

in formula (d') can be in the 2, 3 or 4 position of the dihydroquinoline ring system;

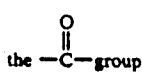

in formula (g') can be in the 1, 3 or 4 position of the dihydroisoquinoline ring system; and $R_1$ is $C_1$-$C_7$ alkyl, $C_1$-$C_7$ haloalkyl or $C_7$-$C_{10}$ aralkyl.

In accord with the present invention, the sustained delivery of a dopaminergic agent to the brain in sufficient concentrations to achieve the desired pharmacological effect can be accomplished with much lower concentrations in the peripheral circulation and other tissues.

The novel chemical delivery system of this invention begins with the preparation of the novel quaternary intermediates of formula (II). The preparation of those intermediates will be tailored to the particular drug portion and carrier portion to be combined. Acyl or carbonate protecting groups may be introduced to protect the catechol hydroxyls, when desired, as already discussed above. Also as discussed hereinabove, the sequence of reaction steps, reactants, solvents, reaction conditions, etc. can be varied, as would be readily apparent to those skilled in the art. Moreover, insofar as concerns the quaternary compounds, when an anion different from the one obtained is desired, the anion in the quaternary salt may be subjected to anion exchange via an anion exchange resin or, more conveniently, by use of the method of Kaminski et al, Tetrahedron, Vol. 34, pp. 2857-2859 (1978). According to the Kaminski et al method, a methanolic solution of an HX acid will react with a quaternary ammonium halide to produce the methyl halide and the corresponding quaternary. X salt.

Thus, a wide variety of synthetic approaches can be utilized, depending on the desired structure of the final product. Various illustrative synthetic schemes in accord with this invention are set forth below in the section entitled "Illustrative Synthetic Methods". While the sequence of reaction steps can be varied in many cases, in general the final step (except in the case of optional salt formation) will be reduction of a quaternary compound of formula (II) to the corresponding dihydro compound of formula (I). The reduction is usually conducted at a temperature from about −10 C. to room temperature, for a period of time from about 10 minutes to 2 hours, conveniently at atmospheric pressure. Typically, a large excess of reducing agent is employed, e.g., a 1:5 molar ratio of reducing agent to starting [D-QC]+ compound. The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product [D-DHC] is usually insoluble in water and thus can be readily separated from the reaction medium. In the case of sodium borohydride reduction, an organic reaction medium is employed, e.g., a lower alkanol such as methanol, an aqueous alkanol or other protic solvent.

Suitable nontoxic pharmaceutically acceptable carriers for use with the topic compounds [D-DHC], e.g., those less toxic than dopamine itself, will be apparent to those skilled in this art. Compare, for example Remington's Pharmaceutical Science, 4th Edition (1970). Obviously, the choice of suitable carriers will depend upon the exact nature of the particular dosage form selected and the identity of the compound to be administered. The therapeutic dosage ranges for administration of the compounds according to this invention will generally, on a molar basis, be the same as, or less than, those which would characteristically be used in this art for administration of the dopamine species [D], per se, (e.g. via L-DOPA) or for administration of other known dopaminergic agents for treatment of like conditions. Naturally, such therapeutic dosage ranges will vary with the size of the patient, the condition for which the [D-DHC] compound is administered, the particular dosage form employed, and the like. The quantity of given dosage form needed to deliver the desired dose of dopamine will of course depend upon the concentration of [D-DHC] in any given pharmaceutical composition/dosage form thereof. In any event, the amount given will be sufficient to elicit a sustained and brain-specific dopaminergic (e.g. anti-hyperprolactinemia or anti-Parkinsonism) response in the animal to which the composition/dosage form is administered.

The ability of the topic compounds to cross the BBB and to be "locked into" the brain allows administration of the drug in a site-specific manner. A combination of the present dihydropyridine⇌pyridinium salt redox system with a sustained release system will further enhance this site-specificity. Thus, a prefered embodiment of the invention comprises formulating the [D-DHC] compound or the salt of the [D-DHC] compound utilizing a sustained release carrier system and/or route of administration capable of slowly releasing the chemical, e.g. sustained release tablets and capsules for oral administration; subcutaneous injection, or implantation of drugs in solid pellet form (for example, distributed in a biodegradable polymer); intramuscular injection of the compound in solution in oil or suspended in a repository vehicle; a transdermal delivery device or form such as an ointment to be applied locally to the desired site (when the drug is susceptible of delivery through the skin), slow intravenous infusion and the like. The rate of release of compound from the sustained release system should be comparable to the rate of in vivo oxidation of the dihydro form of the redox sysrem in order to achieve the greatest degree of enhancement of specificity.

The following synthetic schemes illustrate various approaches to the preparation of the compounds of this invention.

ILLUSTRATIVE SYNTHETIC METHODS

Method A

Dopamine is reacted with nicotinoyl chloride, with nicotinic anhydride, or with nicotinic acid in the presence of a suitable coupling agent such as dicyclohexylcarbodiimide, in an appropriate organic solvent, to afford the corresponding nicotinamide. The nicotinamide is then quaternized, typically by treatment with methyl iodide in a suitable organic solvent, to afford the quaternary derivative of formula (II), which is then reduced by treatment with sodium dithionite or sodium borohydride as generally described hereinabove to afford the desired compound of formula (I).

The foregoing procedure may be repeated using picolinic acid or its acid chloride or anhydride, or isonicotinic acid or its acid chloride or anhydride, in place of nicotinic acid or its acid chloride or anhydride, respectively, to convert dopamine to the corresponding picolinamides and isonicotinamides and then to the corresponding compounds of formulas (II) and (I).

Alternatively, dopamine may be reacted with an activated ester of nicotinic acid, picolinic acid or isonicotinic acid, e.g. a succinimidyl ester such as

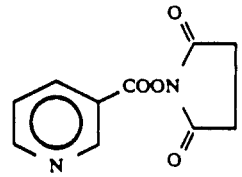

or the phthalimidyl ester corresponding, and the procedure described above repeated to afford the identical products. As yet another alternative, the activated ester, e.g. the succinimidyl ester depicted above, may be quaternized (e.g. by treatment with methyl iodide) and the quaternized activated ester then reacted with dopamine. The quaternary compound of formula (II) thus obtained may then be reduced as described in the first paragraph of this method to give the corresponding compound of formula (I). As still another alternative, the desired anhydride, e.g. nicotinic anhydride, is first reacted with a 2 molar excess of alkyl halide, e.g. methyl iodide, to afford the corresponding quaternized anhydride. The quaternized anhydride is then reacted with dopamine to give the formula (II) quaternary, which may then be reduced as described above to afford the corresponding compound of formula (I).

Method B

This is a variation of Method A used when one or more OH functions in dopamine are to be protected.

Dopamine is first reacted with excess trimethylacetyl chloride to convert the hydroxy group(s) to pivalyloxy group(s). (This process is generally conducted in the presence of a base; however, strongly acid conditions are used when an amine function is present.) That protected derivative is then used as the starting material and subjected to any of the variations in Method A. Alternatively, the first two steps may be reversed, i.e. dopamine may be first converted to the nicotinamide, which may then be reacted with trimethylacetyl chloride to form the protected nicotinamide. As yet another alternative, the dihydroxy formula (II) intermediate obtained via Method A may be reacted with trimethylacetyl chloride and then reduced to the formula (I) compound.

Various other hydroxy protecting groups may be introduced in similar fashion.

Method C

Method A is followed, except that in the first step, dopamine is reacted with 3-quinolinecarboxylic acid or its acid chloride or anhydride or activated ester or quaternized activated ester or quaternized anhydride, instead of nicotinic acid or its acid chloride or anhydride or activated ester or quaternized activated ester or quaternized anhydride.

Similarly, Method C may be combined with any of the variations of Method B to afford the corresponding protected derivatives.

The general procedures described above may be utilized to provide the 1,2-dihydro derivatives as well as the 1,4-dihydros.

The foregoing procedure can be repeated using 4-isoquinolinecarboxylic acid or its acid chloride or anhydride or activated ester or quaternized activated ester or quaternized anhydride in place of 3-quinolinecarboxylic acid or its acid chloride or anhydride or activated ester or quaternized activated ester or quaternized anhydride and, if desired, adapted to the preparation of the protected derivatives as well as the unprotected derivatives.

Method D

Method A is followed, except that a reactant of the formula

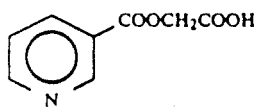

is used in place of nicotinic acid. (That starting material may be prepared by reacting nicotinic anhydride, nicotinoyl chloride or nicotinic acid with glycolic acid.)

Similarly, Method D may be combined with Method B to afford the corresponding protected derivatives.

The foregoing procedure can be repeated using picolinic acid or its acid chloride or anhydride, or isonicotinic acid or its acid chloride or anhydride, in place of nicotinic acid or its acid chloride or anhydride, respectively, in the preparation of the reactant depicted above. This variation affords a reactant of the formula

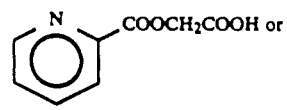 or

which can then be used in place of nicotinic acid to prepare the protected or unprotected derivatives.

Method E

Method A is followed, except that a reactant of the formula

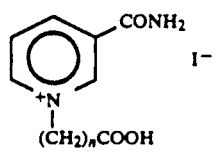

wherein n=1-3, preferably 2, is used in place of nicotinic acid. (That starting material may be prepared from nicotinamide, e.g. when n=2, by reacting 3-iodopropionic acid with nicotinamide.) The quaternary salt of formula (II) thus obtained may then be reduced as described in Method A.

Similarly, Method E may be combined with Method B to afford the corresponding protected derivatives.

The foregoing procedure can be repeated using picolinamide or isonicotinamide in place of nicotinamide in the preparation of the starting material. This variation affords a reactant of the formula

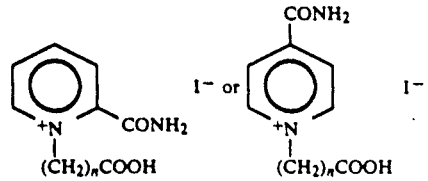

which can then be used in place of nicotinic acid in the procedure of this method, to afford the corresponding protected or unprotected derivatives.

Method F

An ether solution of a compound of formula (I) is treated with an equivalent amount of anhydrous p-toluenesulfonic acid dissolved in dry ether. Mixing at room temperature is continued until the imminium salt precipitates out of solution. The salt is then removed by filtration.

In order to further illustrate the present invention and the advantages thereof, the following specific examples are given, it being understood that same are intended only as illustrative and in nowise limitative.

In the examples immediately to follow, all melting points were taken on a Mel-Temp apparatus and are not corrected. Elemental analyses were performed at Atlantic Microlab, Inc., Atlanta, Georgia. Infrared spectra were determined using a Beckman Acculab 1 double-beam recording spectrophotometer. NMR spectra were determined by menas of a Varian T60A or FX100 spectrometer. All chemical shifts reported are in $\delta$ units (parts per million) relative to tetramethylsilane. Ultraviolet absorbance spectra were determined using a Cary Model 219 spectrophotometer. HPLC analyses were perfomed on a Waters Associates Liquid chromatograph with a Model 6000A solvent delivery system, Model U6K injector and Model 440 absorbance detector. And in all cases where Anal. C, H, N is indicated, the elementary analysis of the compound was found within ±0.4 of the calculated value.

EXAMPLE 1

Preparation of N-Nicotinoyldopamine (compound 7)

To a pyridine solution containing 11.7 g (0.05 mol) dopamine hydrobromide and 6.15 g (0.05 mol) nicotinic acid at 0° C. were added 10.3 g (0.05 mol) dicyclohexylcarbodiimide (DCC). The reaction mixture was stirred at room temperature for 24 hours and the formed dicyclohexylurea was removed by filtration. The pyridine was removed in vacuo and the residue was crystallized from water at 0° C. The product was isolated by filtration and dried over phosphorous pentoxide. Recrystallization from isopropanol gave 9.0 g (0.035 mol), 70% N-nicotinoyldopamine, m.p. 159°-162° C.; aqueous solution of the compound gave a green color with $Fe^{+3}$ and reduced $AgNO_3$; ir (KBr) 3300, 2960, 1725, 1630, 1590, 1520, 1430, 1290, 1190, 1115, 720 and 710 cm$^{-1}$; NMR (d$_6$-DMSO) $\delta$9.25-6.25 (m, 7H), 3.3 (m, 2H) and 2.65 (m, 2H) ppm. Anal. ($C_{14}H_{14}N_2O_3$) C, H, N.

EXAMPLE 2

Preparation of 3-{N-[β-(3,4-Diacetoxyphenyl)ethyl]}carbamoylpyridine

To an ice cold suspension of 2.06 g (8 mmol) finely powdered nicotinoyldopamine in 50 ml of chloroform, 1.56 g (10 mmol) of acetyl chloride were dropped while stirring. The mixture was refluxed for 3 hrs, then filtered. The filtrate was washed with water until the washing did not give test for chloride ions with $AgNO_3$ T.S. Chloroform was distilled on rotavap and the residue was crystallized from ether/pet. ether. Yield 2.2 g (81%) NMR (CDCl$_3$) 8.90 (bs, 1H, C$_2$ pyridine proton), 8.56 (bd, 1H, C$_6$ pyridine proton), 8.16-7.83 (m, 1H, C$_4$ pyridine proton), 7.36-7.03 (m, 5H, C$_6$H$_3$+C$_5$ pyridine proton—NH), 3.60 (q, 2H, J=7 Hz, —N—CH$_2$), 2.90 (t, 2H, J=7 Hz, —CH$_2$).

EXAMPLE 3

Preparation of 3-{N-[β-(3,4-Dipivalyloxyphenyl)ethyl]}carbamoylpyridine (compound 8c)

To a suspension of 5.16 g (0.02 mol) finely powdered nicotinoyldopamine in 100 ml chloroform, 7.23 g (0.06 mol) trimethylacetyl chloride were added under stirring. The mixture was refluxed for 6 hours and then filtered. The filtrate was washed with water free of chloride ions, then washed once with a 5% solution of $NaHCO_3$, then with water. The chloroform was evaporated and the residue was chromatographed by using a silica gel G column and 2% methanol in chloroform as the eluent. The first fraction was collected and evaporated and the residue was crystallized from ether/petroleum ether. Yield, 6.2 g (73%) of a white crystalline solid, m.p. 112°-114° C., NMR (CDCl$_3$) $\delta$9.06 (bs, 1H, C$_2$ pyridine proton), 8.73 (bd, 1H, C$_6$ pyridine proton) 8.30-8.13 (m, 1H, C$_4$ pyridine proton), 7.46-7.10 (m, 5H, C$_6$H$_3$+C$_5$ pyridine proton+CONH), 3.66 (q, 2H, J=6.25 Hz, —N—CH$_2$), 3.0 (t, 2H, J=6 Hz, —CH$_2$), 1.41 [s, 18H, 2—C(CH$_3$)$_3$]. Anal. Calcd for $C_{24}H_{30}N_2O_5$: C, 67,58; H, 7.09; N, 6.56. Found: C, 67.61; H, 7.10; N, 6.54.

EXAMPLE 4

Preparation of 1-Methyl-3-{N-[β-(3,4-dihydroxyphenyl)ethyl]}carbamoylpyridinium iodide (compound 6a)

To a solution of 1.26 g (5 mmol) of nicotinoyldopamine 7 in 10 ml of acetone, 1.41 g (10 mmol) of methyl iodide were added and the mixture was refluxed under stirring for 6 hrs. The acetone was removed and the residue was crystallized from methanol/ether. Yield, 1.7 g (87%), m.p. 155°-157° C. (dec). Aqueous solution gave a green color with $Fe^{+3}$, NMR (D$_2$O) $\delta$9.30-8.28 (ms, 4H, C$_5$H$_4$N$^+$), 7.00 (bs, 3H, C$_6$H$_3$), 4.60 (s, 3H, —N$^+$—CH$_3$), 3.80 (t, 2H, J=7 Hz, —N—CH$_2$), 2.93 (t, 2H, J=7 Hz, CH$_2$). Anal. Calcd for $C_{15}H_{17}IN_2O_3 \cdot H_2O$: C, 43.11; H, 4.55; N, 6.70. Found: C, 43.83; H, 4.23; N, 6.81.

EXAMPLE 5

Preparation of 1-Methyl-3-{N-[β-(3,4-diacetoxyphenyl)ethyl]}carbamoylpyridinium iodide (compound 6b)

To a solution of 1.71 g (5 mmol) of 3-{N-[β-(3,4-diacetoxyphenyl)ethyl]}carbamoylpyridine (prepared like compound 8c), 1.41 g (10 mmol) of methyl iodide were added and the mixture was refluxed overnight under stirring. The acetone solution was then decanted from the insoluble oily residue. Ether was added to the acetone solution and the solid which separated was crystallized from acetone/ether. Yield, 1.9 g (78%) of yellow crystalline needles, m.p. 171°-173° C. U.V. (methanol) 215, 265 nm; NMR (D$_2$O) $\delta$8.86-7.63 (ms, 4H, C$_5$H$_4$N$^+$), 6.66 (bs, 3H, C$_6$H$_3$), 4.4 (s, 3H, —N$^+$—CH$_3$), 3.50 (t, 2H, —N—CH$_2$), 3.03 (t, 2H, CH$_2$), 2.21 (bs, 6H, 2 COCH$_3$). Anal. Calcd for $C_{19}H_{21}IN_2O_5$: C, 47.12; H, 4.37; N, 5.78. Found: C, 47.23; H, 4.38; N, 5.78.

EXAMPLE 6

Preparation of
1-Methyl-3-{N-[β-(3,4-dipivalyloxyphenyl)ethyl]}carbamoylpyridinium iodide (compound 6c)

To a solution of 5.0 g (11.7 mmol) of compound 8c in 20 ml of acetone, 3.3 g (23.4 mmol) of methyl iodide were added and the mixture was refluxed under stirring for 6 hour, then cooled. The orange crystalline solid which separated was filtered, washed with ether and crystallized for acetone/ether. Yield, 5.6 g (85%), m.p. 163°–165° C. U.V. (buffer pH 7.4) 270, 215 nm. NMR (DMSO-$d_6$) δ7.68–7.06 (ms, 7H, $C_5N_4N^+ + C_6H_3 + NH$), 4.56 (s, 3H, $-N^+-CH_3$), 3.42 (q, 2H, J=7 Hz, $-N-CH_2$), 3.19 (t, 2H, J=7 Hz, $CH_2$), 1.32 [s, 18H, $2-C(CH_3)_3$]. Anal. Calcd for $C_{25}H_{33}IN_2O_5$: C, 52.82; H, 5.85; N, 4.92. Found: C, 52.76; H, 5.87; N, 4.90.

EXAMPLE 7

Preparation of
1-Methyl-3-{N-[β-(4-hydroxy-3-methoxyphenyl)ethyl]}carbamoylpyridinium iodide (compound 9)

N-nicotinoyl-3-methoxytyramine was prepared by following the procedure used for the preparation of compound 7. The isolated crude amide was quaternized directly with methyl iodide following the method used for the preparation of compound 6a. Crystallization from methanol gave a yellow crystalline compound, m.p. 192°–194° C. with overall yield of 84%, calculated on the basis of 3-methoxytyramine starting material. NMR ($D_2O$) closely similar to that of 6a except for the singlet at δ3.66 for $OCH_3$.

EXAMPLE 8

Preparation of
1-Methyl-3-{N-[β-(3,4-dihydroxyphenyl)ethyl]}carbamoyl-1,4-dihydropyridine (compound 5a)

To an ice cold solution of 1.0 g (2.5 mmol) of compound 6a in 200 ml of deaerated water, 1.26 g (15 mmol) sodium bicarbonate were added. Nitrogen was bubbled into the mixture and 1.74 g (10 mmol) of sodium dithionite were added gradually to the mixture under stirring. Stirring was continued for 1 hr and the mixture was then extracted twice with 50 ml of ether. The ether extract was washed with water, dried with anhydrous $Na_2SO_4$ and evaporated to dryness. Yield, 0.36 g (54%) of a yellow solid, m.p. 90°–93° C. (dec.) which gave a green color with ferric chloride test and reduced alcoholic $AgNO_3$ instantly. UV ($CH_3OH$) 220, 350 nm. NMR ($CDCl_3/D_2O$) δ7.2–6.9 (ms, 4H, $C_6H_3+C_2$ dihydropyridine proton), 5.6 (m, 1H, $C_6$ dihydropyridine proton), 4.6–4.4 (m, 1H, $C_5$ dihydropyridine proton), 3.4 (m, 2H, $-N-CH_2$), 3.1–2.7 (m, 7H, $N-CH_3 + C_4$ dihydropyridine protons+$CH_2$). Anal. Calcd for $C_{15}H_{18}N_2O_3 \cdot \frac{1}{2}H_2O$: C, 63.59; H, 6.76; N, 9.88. Found: C, 63.56; H, 6.85; N, 9.72.

EXAMPLE 9

Preparation of
1-Methyl-3-{N-[β-(3,4-diacetoxyphenyl)ethyl]}carbamoyl-1,4-dihydropyridine (compound 5b)

To an ice cold solution of 1.4 g (3 mmol) of compound 6b in 200 ml of deaerated water, 1.5 g (18 mmol) of sodium bicarbonate were added. A stream of $N_2$ was bubbled into the mixture and 2.1 g (12 mmol) of sodium dithionite were gradually added under stirring. Stirring was continued for 30 min and then the mixture was extracted with ethyl acetate. The extract was washed with water, dried with anhydrous $Na_2SO_4$ and evaporated to dryness. The yellowish semisolid mass remaining gave a faint green color with ferric chloride test indicating partial hydrolysis of the ester functions. It reduced alcoholic silver nitrate instantly. U.V. ($CH_3OH$) 220, 273 and 355 nm; NMR ($CDCl_3/D_2O$) δ7.13–6.80 (ms, 4H, $C_6H_3+C_2$ dihydropyridine proton), 5.53 (doublet of doublets, 1H, $C_6$ dihydropyridine proton), 4.63–4.46 (m, 1H, $C_5$ dihydropyridine proton), 3.33 (t, 2H, J=6.5 Hz, $-N-CH_2$), 3.06–2.66 (m, 7H, $-N-CH_3 + C_4$ dihydropyridine proton + $CH_2$), 1.8 (s, =6H, $2COCH_3$).

EXAMPLE 10

Preparation of
1-Methyl-3-{N-[β-(3,4-dipivalyloxyphenyl)ethyl]}carbamoyl-1,4-dihydropyridine (compound 5c)

To a cold mixture of 2.0 g (3.5 mmol) of compound 6c, 200 ml of deaerated water and 100 ml of ethyl acetate, 1.14 g (14 mmol) of sodium bicarbonate and 2.43 g (14 mmol) of sodium dithionite were added. The mixture was stirred under $N_2$ for 20 minutes. The ethyl acetate layer was separated and the aqueous layer was reextracted with 100 ml of ethyl acetate. The combined ethyl acetate was washed with cold deaerated water, dried over anhydrous $Na_2SO_4$ and distilled on rotovapor. The viscous yellow oily residue was dissolved in 5 ml of acetone, filtered under $N_2$ atmosphere and then evaporated under reduced pressure. The solid residue was dried under vacuum over $P_2O_5$ in $N_2$ atmosphere. It reduced alcoholic $AgNO_3$ instantaneously and gave no color with $FeCl_3$ test. Yield, 1.3 g (83%) m.p. 45°–48° C.; UV ($CH_3OH$) 210 and 355 nm; NMR ($CDCl_3$) δ7.04–6.92 (m, 4H, $C_6H_3+C_2$ dihydropyridine proton), 5.71–5.61 (doublet of doublets, 1H, $C_6$ dihydropyridine proton), 4.81 (bs, 1H, CONH), 4.60–4.51 (m, 1H, $C_5$ dihydropyridine proton), 3.53 (q, 2H, J=6.3 Hz, $-N-CH_2$), 2.36 (bs, 2H, $C_4$ dihydropyridine proton), 2.91 (s, 3H, $N-CH_3$), 2.79 (t, 2H, J=6.3 Hz, $CH_2$), 1.33 [s, 18H, $CO-C(CH_3)_3$]. Anal. Calcd for $C_{25}H_{34}N_2O_5 \cdot 1\frac{1}{2}H_2O$: C, 63.9; H, 7.93; N, 5.96. Found: C, 63.4; H, 7.81; N, 5.94.

EXAMPLE 11

Preparation of
1-Methyl-3-{N-[β-(4-hydroxy-3-methoxyphenyl)ethyl]}carbamoyl-1,4-dihydropyridine (compound 10)

This compound was prepared following the same method as for the preparation of compound 5c. The crude solid obtained showed the same NMR (CDCl₃/D₂O) pattern as compound 5a, except for a peak at δ3.5 for the OCH₃ protons. It was sufficiently pure for the determination of its retention time following the HPLC method of analysis detailed in EXAMPLE 18 below. No trials were made for its further crystallization or elemental analysis.

EXAMPLE 12

Preparation of 1-Methyl-3-{N-[β-(3,4-dihydroxyphenyl)ethyl]}carbamoylpyridinium iodide To a solution of 2 g (7.7 mmol) of nicotinoyldopamine in 40 ml of dry methanol were added 2.5 g (17.6 mmol) of methyl iodide. The reaction mixture was refluxed with stirring for 6 hours. Methyl iodide (1.5 g, 1.05 mmol) was added and refluxing was continued overnight. Methanol was removed and ethyl acetate was added, affording yellowish crystals of the desired product. Yield 2.4 g (77%), m.p. 173°-174° C.

EXAMPLE 13

Preparation of 1-Methyl-3-{N-[[β-[3,4-bis(isobutyryloxy)phenyl]ethyl]]}carbamoylpyridinium trifluoroacetate To an ice-cold solution of the product of Example 12 (3 g, 7.5 mmol) in 30 ml of trifluoroacetic acid, isobutyryl chloride (2.4 g, 22.5 mmol) was added slowly, with stirring. Stirring was continued overnight at room temperature. Trifluoroacetic acid was evaporated under vacuum and the residue was crystallized from ethyl ether:hexane (3:1). Yield 1.2 g (30.4%), m.p. 87°-91° C.

Substantial repetition of the procedure of the preceding paragraph, substituting trimethylacetyl chloride for the isobutyryl chloride used above, affords after appropriate purification, 1-methyl-3-{N-[β-(3,4-dipivalyloxyphenyl)ethyl]}carbamoylpyridinium trifluoroacetate in 72% yield (4.0 g), m.p. 158°-160° C.

EXAMPLE 14

Preparation of 1-Methyl-3-{N-[[β-[3,4-bis(isobutyryloxy)phenyl]ethyl]]}carbamoyl-1,4-dihydropyridine (compound 5d)

A solution of 0.55 g (1 mmol) of 1-methyl-3-{N-[[β-[3,4-bis(isobutyryloxy)phenyl]ethyl]]}carbamoylpyridinium trifluoroacetate in 50 ml of deaerated water containing 10 ml of methanol was extracted three times with 30 ml portions of ether. To the resultant aqueous solution were added NaHCO₃ (0.25 g, 3 mmol) and 50 ml of ethyl ether and the mixture was kept under nitrogen. To this ice-cold mixture was added sodium dithionite (0.52 g, 3 mmol) and the mixture was stirred vigorously for 30 minutes. The ether layer was separated and the aqueous layer was extracted twice with ether. The combined ether extracts were washed with water and dried over sodium sulfate. Ether was removed under vacuum, leaving an oily product. NMR analysis confirmed that the product has the structural formula:

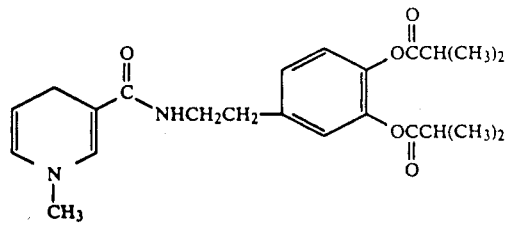

EXAMPLE 15

Preparation of 1-Methyl-3-{N-[β-(3,4-dihydroxyphenyl)ethyl]}carbamoyl-1,4-dihydropyridine (compound 5a)

The product of Example 12 (750 mg, 1.87 mmol) was dissolved in 200 ml of degassed, ice-cold distilled water. N₂ was bubbled through the solution for 5 minutes, after which 1.26 g (15 mmol) of sodium bicarbonate and 1.74 g (10 mmol) of sodium dithionite were added while stirring. After one hour, the mixture was extracted with ether (3×100 ml). The combined organic layers were washed with ice-cold water (100 ml) and dried over anhydrous Na₂SO₄. Removal of solvent under reduced pressure gave 315 mg of the desired dihydro compound, as a sticky yellow foam. Yield 62%.

EXAMPLE 16

Preparation of N-Nicotinoyloxysuccinimide

Nicotinic acid (4.025 g, 0.0327 mol) and N-hydroxysuccinimide (3.763 g, 0.0327 mol) were dissolved in 130 ml of dioxane. Dicyclohexylcarbodiimide (6.75 g, 0.032 mol) in 20 ml of dioxane was added. The reaction mixture was then stirred at room temperature for 3 hours. The dicyclohexylurea which precipitated was removed by filtration and the solvent was removed by rotary evaporation. The crude product was recrystallized from ethyl acetate to give light yellow crystals which were then washed with anhydrous ether. The product, obtained in 72% yield (5.2 g) and melting at 129°-131° C., has the formula:

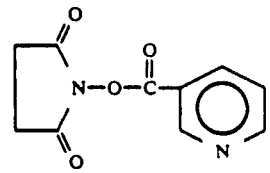

This activated ester may be utilized as a starting material as described in the Illustrative Synthetic Methods hereinabove. Other suitable activated esters may be similarly prepared, e.g. N-hydroxyphthalimide may be used to prepare N-nicotinoyloxyphthalimide.

EXAMPLE 17

Preparation of N-[(1-Methyl-3-pyridinium)carbonyloxy]succinimide iodide

N-Nicotinoyloxysuccinimide (5.0 g, 0.0227 mol) was dissolved in 80 ml of dioxane and methyl iodide (4.24 ml, 0.0683 mol) was added. The reaction mixture was refluxed at 70° C. overnight. The solution changed to a red color while a yellow precipitate formed. The precipitate was removed by filtration, washed thoroughly with anhydrous ether and dried. Yield 87% (7.134 g) of the quaternized product of the formula:

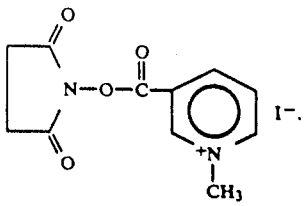

The quaternized activated ester thus obtained may be utilized as a starting material as described in the Illustrative Synthetic Methods hereinabove. Other suitable quaternized esters may be similarly prepared, e.g. from N-nicotinoyloxyphthalimide.

EXAMPLE 18

Analytical Methods

A high pressure liquid chromatography (HPLC) method was developed for the studies of the degradation of the dihydropyridine derivative. The chromatographic analysis was performed on a component system consisting of a Waters Associate Model 6000A solvent delivery system, Model U6K injector and Model 440 dual channel absorbance detector operated at 254 and 280 nm. A 30 cm × 3.9 mm (internal diameter) reverse phase μBondapak $C_{18}$ column (Waters Associates), operated at ambient temperature, was used for all separations. The mobile phase used for the separation of the dihydropyridine derivative, its degradation products and oxidation products consisted of 0.005M solution of 1-heptanesulfonic acid sodium salt (PIC B-7 Eastman Kodak) in $CH_3CN$; 0.01M aqueous dibasic ammonium phosphate (2.5:1). At a flow rate of 2.0 ml/min, 6a had a retention time of 5.1 min; 6c, 11.8 min; 5a, 1.7 min; 5c, 3.1 min. A peak was always shown at a retention time of 2.2 min which is believed to be a monodeacylated dihydropyridine derivative, since it evetually did result in 6a.

EXAMPLE 19

Determination of the Enzymatic Hydrolytic Cleavage and Rate of Oxidation of Compound 5c In Human Plasma:

The freshly collected plasma used was obtained at the Civitan Regional Blood Center, Inc. (Gainesville, Florida) and contained about 80% plasma diluted with anticoagulant citrate phosphate dextrose solution U.S.P. The plasma was stored in a refrigerator and used the next day. One hundred μl of a freshly prepared 0.61M solution of compound 5c in methanol was added to 20 ml of plasma, previously equilibrated to 37° C. in a water bath and mixed throughly to result in an initial concentration of $3.05 \times 10^{-3}$ moles/liter. One ml samples of plasma were withdrawn from the test medium, added immediately to 5 ml of ice-cold acetonitrile, shaken vigorously and placed in a freezer. When all samples had been collected, they were centrifuged and the supernatants were filtered through Whatman 1 filter papers and analyzed by HPLC.

In Human Blood:

The freshly collected heparinized blood was obtained at the Civitan Regional Blood Center, Inc. (Gainesville, Florida). The blood was stored in a refrigerator and used the next day. One hundred μl of a freshly prepared 0.19M solution of compound 5c in methanol was added to 20 ml of blood, previously equilibrated to 37° C. in a water bath and mixed thoroughly to result in a initial concentration of $9 \times 10^{-4}$ moles/liter. One ml samples of blood were withdrawn from the test medium every 5 minutes, added immediately to 5 ml of ice cold acetonitrile, shaken vigorously and placed in a freezer. When all samples had been collected, there were centrifuged and the supernatants were filtered using Whatman 4 filter paper and analyzed by HPLC.

In Rat Brain Homogenate:

The brain homogenate was prepared by the following method. Five Sprague-Dawley rats were killed by decapitation and the brains were removed, weighed (total weight 9.85 g) and homogenized in 49.3 ml of aqueous 0.11M phosphate buffer, pH 7.4. The homogenate was centrifuged and the supernatant was used for the test. 100 μl of 0.18M solution of compound 5c was mixed with 10 ml of homogenate, previously equilibrated to 37° C. in a water bath, to result in an initial concentration of $1.8 \times 10^{-3}$ moles/liter. Samples of 1.0 ml were withdrawn every 10 minutes from the test medium, added immediately to 5 ml of ice cold acetonitrile and placed in a freezer. When all samples had been collected, they were centrifuged. Each supernatant was filtered through two Whatman 1 filter papers and analyzed by HPLC.

In Rat Liver Homogenate:

The liver homogenate was prepared by the following method. Three Sprague-Dawley rats were killed by decapitation and the livers were removed, weighed and homogenized by tissue homogenizer in 0.11M aqueous phosphate buffer, pH 7.4, to make 20% liver homogenate The homogenate was centrifuged and the supernatant was used for the test. 100 μl of 0.1M solution of compound 5c in methanol were mixed with 20 ml of the homogenate, previously equilibrated to 37° C. in a water bath, to result in an initial concentration of $9 \times 10^{-4}$ moles/liter. Samples of 1.0 ml were withdrawn every 5 minutes from the test medium, added immediately to 5 ml of ice cold acetonitrile, shaken vigorously and placed in a freezer. When all samples had been collected, they were centrifuged and each supernatant was filtered through Whatman 1 filter paper and analyzed by HPLC.

Rates of disappearance (overall oxidation and degradation) of compound 5c:
 (i) In Plasma:
  $R = 2.25 \times 10^{-4} \text{ sec}^{-1}$
  $t_{\frac{1}{2}} = 51.3 \text{ min}$
  $r = 0.998$
  $n = (3 \times 6)$
 (ii) In 20% Brain Homogenate:
  $R = 6.7 \times 10^{-4} \text{ sec}^{-1}$
  $t_{\frac{1}{2}} = 17.2 \text{ min}$
  $r = 0.996$ n=(3×6)
(iii) In Blood:
 $R = 6.3 \times 10^{-4}$
 $t_{\frac{1}{2}} = 18.2$ min
 $r = 0.997$
 $n = (3 \times 7)$
(iv) In Liver:
 $R = 1.93 \times 10^{-3}$
 $t_{\frac{1}{2}} = 5.9$ min
 $r = 0.950$
 $n = (3 \times 5)$

EXAMPLE 20

Determination of Concentration of Compound 6a in Brain and Blood after Parenteral Administration of 5c Male Sprague-Dawley rats of average weight of 150±10 g were used. The rats were anesthetized with IM injection of Inovar and the jugular was exposed. Compound 5c was injected intrajugularly in the form of 10% solution in DMSO at a dose of 64.2 mg/kg (equivalent to 50 mg/kg compound 6a). The injection was given at a rate of 24 μl/min using a calibrated infusion pump. After appropriate time periods, 1 ml of blood was withdrawn from the heart and dropped immediately into a tared tube containing 3 ml acetonitrile, which was afterwards weighed to determine the weight of the blood taken. The animal was then perfused with 20 ml of saline solution and decapitated and the brain was removed. The weighed brain was homogenized with 0.5 ml of distilled water, 3 ml of acetonitrile were added and the mixture was rehomogenized thoroughly, centrifuged, filtered and then analyzed for compound 6a using the HPLC method. The tubes containing the blood were shaken vigorously, centrifuged, decanted and also analyzed for compound 6a using the HPLC method. Quantitation was done by using a recovery standard curve obtained by introducing a known amount of 6a in either brain homogenate or blood and then treating in the same manner. See FIG. 6 and the discussion thereof hereinabove.

EXAMPLE 21

Pharmacological Studies

In vivo effect on pituitary prolactin secretion:
Adult male rats (Charles Rivers, CD-1) weighing 200 to 225 g were provided food and water ad libitum for at least one week prior to experimentation. To elevate serum prolactin levels, each rat received a single s.c. implant of a Silastic tube (1.57 mm interior diameter, 5 mm×3.15 mm overall size) packed with crystalline 17β-estradiol. Two days later the rats were lightly anesthetized with ether and a small incision was made over the right jugular vein for intravenous (I.V.) administration of the test drugs. Compound 6a was injected at a dose of 1 mg/kg body weight/ml saline and groups of six rats were decapitated at 15, 30, 60 and 120 minutes later to collect blood samples. Control rats (time 0) received an I.V. injection of the saline vehicle and were decapitated 30 minutes later. Compound 5c was dissolved in 10% ethanol in saline and was injected I.V. Rats were decapitated at 15, 30 and 120 minutes later. Control (time 0) animals received the 10% ethanol vehicle and were sampled 30 minutes later.

Trunk blood was collected, allowed to clot for 2 hours and the serum was separated and stored at 20° C. for subsequent assay for prolactin concentrations. Each serum sample was assayed in duplicate by the double-antibody radioimmunoassay procedure described by the National Hormone and Pituitary Program of NIADDK (National Institute on Arthritis, Diabetes and Digestive and Kidney Diseases). Serum prolactin concentrations are expressed in terms of the PRL-RP-2 reference preparation provided. The intraassay coefficient of variation for 10 replicate samples of pooled serum obtained from male rats was 13.8%.

The effects of compounds 5c and 6a on serum prolactin concentrations were evaluated by one-way analysis of variance and Student-Newman Keuls tests. A probability level of less than 0.05 was selected for significance. See FIG. 7 and the discussion thereof hereinabove.

The foregoing procedure was repeated, except for the following changes:

Compound 5c (the dihydropyridine dipivalyl ester derivative of dopamine) was dissolved in 10% dimethylsulfoxide in saline and administered intravenously at a dosage of 1 mg/kg to groups of five or six rats; the rats were decapitated at 1, 2, 4, 8, 12 and 24 hours following administration. Compound 5a (the dihydropyridine dihydroxy derivative) was dissolved in 10% dimethylsulfoxide and administered intravenously at a dosage of 1 mg/kg to groups of six rats; the rats were decapitated at 1, 2 and 4 hours after administration. Control groups of animals received 10% dimethylsulfoxide in saline and were sacrificed 2 hours later. Intravenous administration of 5c was found to maintain a dramatic reduction in serum prolactin concentrations for at least 12 hours following administration. Again, the rapid onset and very prolonged inhibitory effects of 5c on prolactin secretion is consistent with the time course of the appearance of 6a in the brain following administration of 5c and the "trapping" of 6a in the brain. Compound 5a did produce a significant reduction in serum prolactin concentration at 2 hours, but by 4 hours the prolactin levels had increased substantially; thus 5a did not show as prolonged an inhibitory efect as that exhibited by 5c.

The general procedure detailed above was again repeated for compound 5c. Adult male rats (Charles River CD, 225-250 g) received a single subcutaneous implant packed with crystalline 17β-estradiol. Two days later, the rats were given a single intravenous injection (jugular vein) of compound 5c (1 mg/kg) in 10% dimethylsulfoxide. Serum samples were analyzed in duplicate by a double-antibody radioimmunoassay procedure described in the National Hormone and Pituitary Program of NIADDK. The intraassay coefficient of variation for 10 replicate samples of pooled serum obtained from male rats was 11.9%. The effects of compound 5c on serum prolactin concentrations were evaluated by one-way analysis of variance and the Student-Newman Keuls test. *, $p<0.025$; , $p<0.01$; *, $p<0.005$. The effects of compound 5c on serum prolactin concentration over a 12 hour period are depicted in FIG. 8. Serum prolactin levels at 24 hours after administration of 5c were 154±30 ng/ml.

In vitro evaluation of the prolactin inhibitory effect of 6a:

Adult female rats (Charles Rivers Lab.) weighing 225-250 g were maintained on food and water ad libitum. Animals were sacrificed by decapitation; their pituitary glands were quickly removed from the cranium. The anterior pituitary (AP) of each animal was dissected into two equal halves and placed into incubation media. (Gibco's Minimal Essential Media supplied by Grand Island Biological Co. was used.) The incubation was conducted at 37° C., under continuous aeration (95% $O_2$, 5% $CO_2$); the pH was 7.2. After one hour of preincubation, the media were discarded and replaced with fresh ones containing either DA ($2 \times 10^{-8}$M), 6a ($2 \times 10^{-8}$M) or ascorbic acid ($10^{-4}$M). In all cases, one-half of AP received the test drug; the other, the ascorbate control. After one hour, samples were taken from the media and the remaining media were discarded. Fresh media containing DA ($2 \times 10^{-7}$), 6a ($2 \times 10^{-7}$) and ascorbate, respectively, were then added. One hour later, then second samples were taken. After the 3 hour incubation period, each half AP's were weighed.

The samples were diluted 1:50 with phosphate buffered saline and then assayed in triplicate by the radioimmunoassay method described. The data are given as ng prolactin released/mg wet weight/hour. Paired Student's T-test was used to evaluate the significance of the inhibitory effects of the test drugs on prolactin secretion. The control AP half and the drug treated half were employed in each paired comparison. See TABLE I and the discussion thereof hereinabove.

Further in vitro evaluation of the prolactin inhibitory effect of 6a vs. dopamine:

Eighteen female rats (Charles Rivers Lab.) weighing 225-250 g were maintained on food and water ad libitum for one week. Animals were sacrificed by decapitation, the pituitary gland was removed from the cranium and the anterior pituitary (AP) was separated from the posterior and intermediate lobes. The AP was dissected into two equal halves and each half was placed in an incubation media consiting of Gibco's Minimal Essential Media containing 25 mM Hepes Buffer (Grand Island Biological Company, Grand Island, New York). The media was maintained at a pH of 7.2 under continuous aeration (95% $O_2$, 5% $CO_2$) at a temperature of 37° C. Following a one hour preincubation period, the media were discarded and replaced with fresh media containing either DA ($10^{-6}$M) or 6a ($10^{-6}$M). The control AP half received media containing $10^{-4}$M ascorbic acid, the vehicle for the drugs. After one hour, the media were sampled and the remaining media were discarded. Fresh media containing DA ($10^{-5}$M) or 6a ($10^{-5}$) or ascorbic acid ($10^{-4}$M) were then added to the AP halves. One hour later, second samples were taken and the AP halves were weighed to the nearest tenth of a milligram.

Samples of media were diluted 1:50 with phosphate buffered saline and then assayed in triplicate by radioimmunoassay methods. Data are expressed as ng prolactin released/mg net weight/h. Paired student's "t" tests were used to evaluate the significance of the effects of the drugs on the prolactin release rate. The control AP half and its respective drug-treated AP half were employed in each paired comparison. The results are tabulated below:

| | Prolactin ng/mg/h | | | | | | |
|---|---|---|---|---|---|---|---|
| Dopamine (DA) | | | | 6a | | | |
| Control | DA ($10^{-6}$M) | Control | DA ($10^{-5}$M) | Control | 6a ($10^{-6}$M) | Control | 6a ($10^{-5}$M) |
| 306 ± 50 | 128 ± 22 | 219 ± 26 | 59 ± 20 | 349 ± 49 | 301 ± 51 | 206 ± 25 | 206 ± 28 |

Thus, control AP halves released prolactin at a rate of 300 to 350 ng/mg wet weight/hour during the first incubation period and about 200 ng/mg wet weight/hour during the second incubation period. Dopamine (DA) concentration of $10^{-6}$ and $10^{-5}$M caused a 58 and 73% decrease in prolactin secretion, respectively. In contrast, M-methylnicotinoyldopamine 6a did not alter the rate of prolactin secretion at concentrations of $10^{-6}$ or $10^{-5}$M. These results confirm the conclusions drawn from the earlier studies which were done at lower concentrations.

EXAMPLE 22

Further Pharmacological Studies

Figure 9:
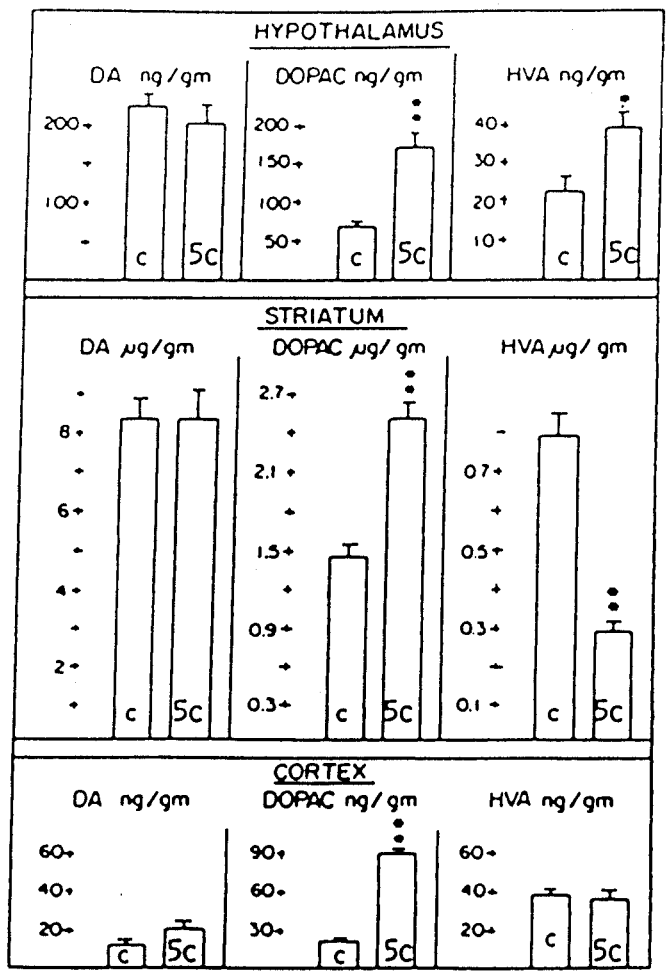
FIG. 9 consists of bar graphs showing the concentrations of dopamine (DA), dihydroxyphenylacetic acid (DOPAC) and homovanillic acid (HVA) in several brain regions after administration of compound 5c.

Method A:

Male Sprague-Dawley rats weighing 225 to 250 g were given an intrajugular injection of 5c (50 mg/kg) or the vehicle, dimethylsulfoxide. The monoamines and metabolites were determined by high-performance liquid chromatography using amperometric methods. The coefficients of variation for the assays were 6.0% for DOPAC (dihydroxyphenylacetic acid) and 9.4% for HVA (homovanilic acid). The concentrations of DA, DOPAC and HVA in several brain regions which were determined are shown in FIG. 9. The data presented are expressed as mean±SEM for 5 to 6 animals per group. A single asterisk indicates $p < 0.025$ and two asterisks indicate $p < 0.001$.

Method B:

Male rats weighing 200-220 g were given an intravenous (tail vein) injection of DA (2.7 mg/kg, 5c or 5d (30 mg/kg) or vehicle (60% dimethylsulfoxide in saline). At a molar dose of DA (10.7 mg/kg) equivalent to that of 5c or 5d, all 5 animals died. Hence, the DA dose was reduced 75%. Thirty minutes later, animals received an i.p. injection of m-hydroxybenzylhydrazine (NSD 1015, 100 mg/kg) in saline. Exactly 30 minutes later, the animals were killed by decapitation, and the tissues were dissected, weighed and stored frozen. DA, DOPAC and HVA were separated by gas chromatography and quantitated by mass spectrometry using deuterated internal standards [Eng, Life Sci. 29, 2227 (1981); Karoum et al, J. Neurochem. 25, 653 (1975)]. The effects of this blockade of endogenous dopamine synthesis on concentrations of DA, DOPAC and HVA in several brain regions are shown in FIG. 10. The data presented are expressed as mean±SEM for 7 to 13 animals per group. The asterisk indicates p<0.02.

Method C:

The procedure used to evaluate the role of MAO in the processing of the instant delivery system using pargyline to block MAO activity is described fully in the text hereinabove which precedes the Illustrative Synthetic Methods.

Accordingly, provided hereby are not only a generic method and novel class of pro-prodrugs for the specific and/or target enhanced delivery of dopamine to the brain via the bidirectional transport of the drug species into and out of the brain employing dihydropyridine pyridinium salt carrier redox systems, but also a system providing insight into the basic transport processes (both active and passive) of, and enzymatic activities in, the blood-brain barrier, as well as into the various processes specific to the function of the brain. Again, another very significant aspect of the bioreversible redox delivery system according to this invention is the toxicity implication, for significantly reduced is systemic toxicity by accelerating the elimination of the drug/quaternary carrier system. And even central toxicity is reduced by providing for low level, sustained release of the active drug species in the brain. Low toxicity is provided both as regards the quaternary carrier and in combination with the drug. Again, the present invention is not based on a simple prodrug, as was the case with the earlier work done with 2-PAM. In that case, a hydrophilic compound (2-PAM) was made lipoidal by making its dihydropyridine form (Pro-2-PAM) to enable its penetration through lipoidal barriers. This allowed the compound to get into the brain as well as other organs, but this prodrug manipulation did not and could not result in any brain specificity. And while the possibility of carrying drugs to the brain was also hypothesized earlier, all the experimental evidence reported in the literature negates any possible specificity, for the only compound delivered to the brain (2-PAM via Pro-2-PAM) showed similar efflux properties from the brain as from the other organs. There is no suggestion in the art of the brain-specific delivery which has now been achieved and which is a result of a surprisingly slow in vivo oxidation of the dihydro carrier system compared to the one reported in the earlier 2-PAM⇌Pro-2-PAM system. Indeed, a most surprising and unexpected feature of the present delivery system is that it will result in a build-up of the concentration of the intermediate charged species (quaternary form) in the brain even after one single bolus injection of the starting lipophilic chemical delivery sytem (dihydro form). There is a first portion of the brain level versus time curve which shows a significant increase in the brain (up to doubling or even more) from the starting overall concentration, and this process takes place against the concentration gradient; see, for example, FIG. 6. The blood levels do simultaneously fall, and after some time (for example, for 1 to 1½ hours) significantly higher concentrations of the precursor, now in its hydrophilic carrier (quaternary) form, will be found in the brain as compared to the rest of the body. This is brain-specific delivery; it is not simply delivery of something which otherwise cannot get to the brain, but is delivery of a given agent in an inactive form specifically to the brain, which then will subsequently lead to a sustained brain-specific delivery of the active specie itself. Thus, slow enzymatic cleavage of the quaternary form "locked in" the brain provides sustained release of dopamine itself.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A compound having the formula

[D—DHC]  (I), or a non-toxic pharmaceutically acceptable salt thereof, wherein [D] is a dopamine having the structural formula

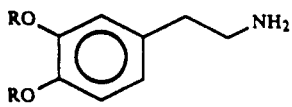

in which each R is independently hydrogen or a hydrolytically or metabolically cleavable hydroxyl protective group, and [DHC] is the reduced, biooxidizable, blood-brain barrier penetrating, lipoidal form of a dihydropyridine⇌pyridinium salt redox carrier.

2. A compound as defined by claim 1, wherein:
   (a) at least one R is hydrogen; or
   (b) both R's are hydrogen; or
   (c) at least one R is an acyl group; or
   (d) both R's are acyl groups; or
   (e) at least one R is a carbonate group; or
   (f) both R's are carbonate groups.

3. A compound as defined by claim 1, wherein:
   (a) one R is pivalyl and the other R is hydrogen or pivalyl; or
   (b) one R is isobutyryl and the other R is hydrogen or isobutyryl; or
   (c) one R is ethoxycarbonyl and the other R is hydrogen or ethoxycarbony; or
   (d) one R is isopropoxycarbonyl and the other R is hydrogen or isopropoxycarbonyl.

4. A compound as defined by claim 1, wherein [DHC] is

-continued
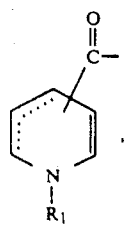
(a')
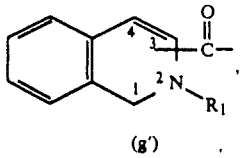
(g')
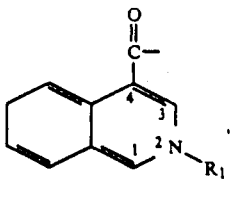
(g")
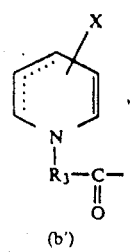
(b')
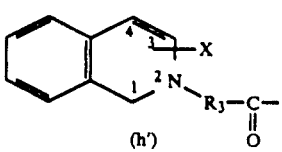
(h')
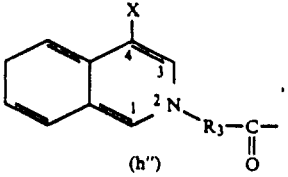
(h")
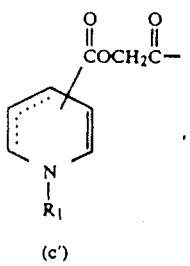
(c')
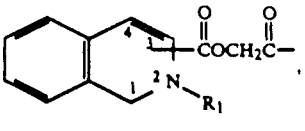
(j')
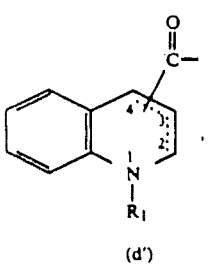
(d')
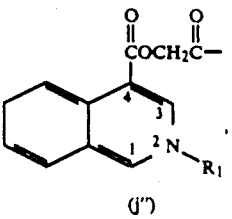
(j")
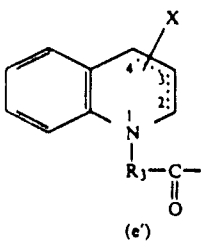
(e')
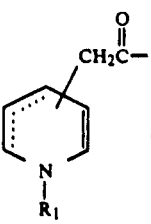
(k')
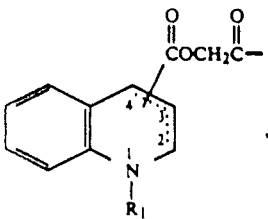
(f')
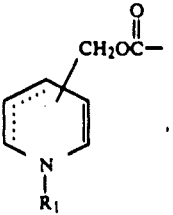
(l')

-continued

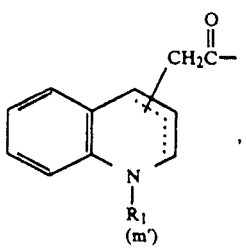
(m')

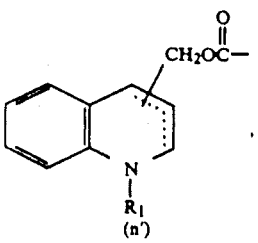
(n')

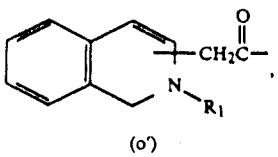
(o')

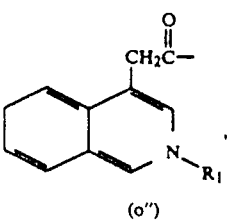
(o'')

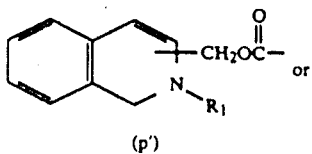
(p') or

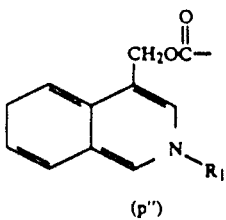
(p'')

wherein the dotted line in formulas (a'), (b'), (c'), (k') and (l') indicates the presence of a double bond in either the 4 or 5 position of the dihydropyridine ring; the dotted line in formulas (d'), (e'), (f'), (m') and (n') indicates the presence of a double bond in either the 2 or 3 position of the dihydroquinoline ring system; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R", wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a'), (c'), (k') and (l') and the X substituent in formula (b') can each be attached at the 2, 3 or 4 position of the dihydropyridine ring; the carbonyl-containing groupings in formulas (d'), (f'), (m') and (n') and the X substituent in formula (e') can each be attached at the 2, 3 or 4 position of the dihydroquinoline ring system; and the carbonyl-containing groupings in formulas (g'), (j'), (o') and (p') and the X substituent in formula (h') can each be attached at the 1, 3 or 4 position of the dihy-droisoquinoline ring system.

5. A compound as defined by claim 1, wherein [DHC] is

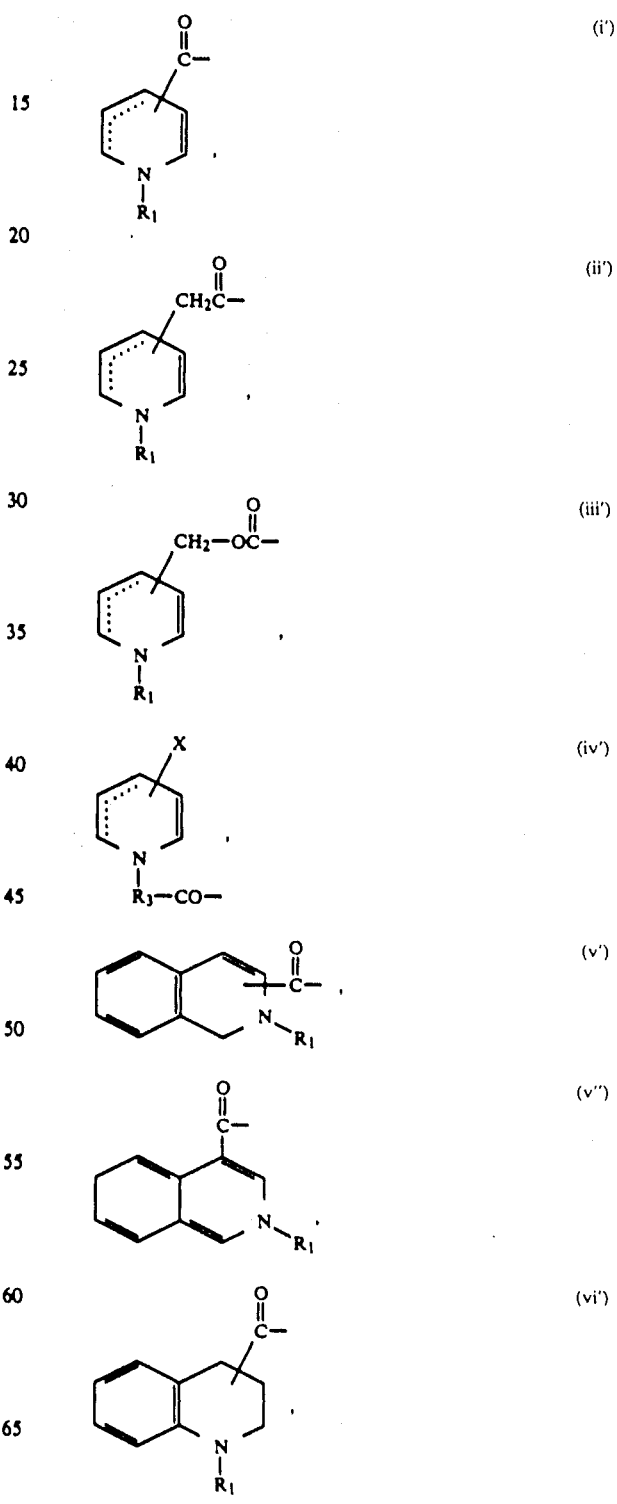

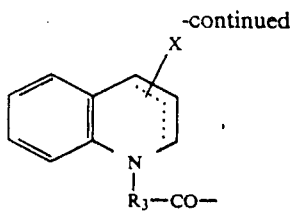

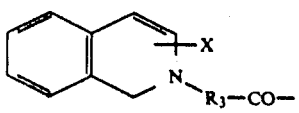

or

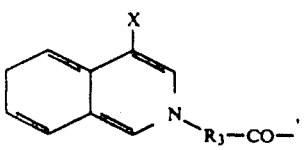

wherein the dotted line in formulas (i'), (ii'), (iii') and (iv') indicates the presence of a double bond in either the 4 or 5 position of the dihydropyridine ring; the dotted line in formulas (vi') and (vii') indicates the presence of a double bond in either the 2 or 3 position of the dihydroquinoline ring; $R_1$ is $C_1-C_7$ alkyl, $C_1-C_7$ haloalkyl or $C_7-C_{10}$ aralkyl; $R_3$ is $C_1-C_3$ alkylene; X is —CONR'R'', wherein R' and R'', which can be the same or different, are each H or $C_1-C_7$ alkyl, or X is —CH=NOR''' wherein R''' is H or $C_1-C_7$ alkyl; the carbonyl-containing groupings in formulas (i'), (ii') and (iii') and the X substituent in formulas (iv') can each be attached at the 2, 3 or 4 position of the dihydropyridine ring; the carbonyl-containing grouping in formula (vi') and the X substituent in formula (vii') can each be attached at the 2, 3 or 4 position of the dihydroquinoline ring system; and the carbonyl-containing grouping in formula (v') and the X substituent in formula (viii') can each be attached at the 1, 3 or 4 position of the dihydroisoquinoline ring system.

6. A compound as defined by claim 1, wherein [DHC] comprises the reduced form of an N-substituted nicotinic acid derivative or of an N-substituted isoquinoline, particularly of a trigonelline.

7. A compound as defined by claim 1, wherein [DHC] is

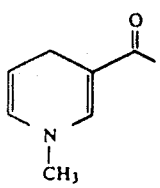

8. A compound having the formula

[D-QC]+ (II)

wherein [D] is a dopamine having the structural formula

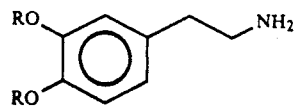

in which each R is independently hydrogen or a hydrolytically or metabolically cleavable hydroxyl protective group, and [QC]+ is the hydrophilic, ionic pyridinium salt form of a dihydropyridine⇌pyridinium salt redox carrier.

9. A compound as defined by claim 8, wherein:
(a) at least one R is hydrogen; or
(b) both R's are hydrogen; or
(c) at least one R is an acyl group; or
(d) both R's are acyl groups; or
(e) at least one R is a carbonate group; or
(f) both R's are carbonate groups.

10. A compound as defined by claim 8, wherein:
(a) one R is pivalyl and the other R is hydrogen or pivalyl; or
(b) one R is isobutyryl and the other R is hydrogen or isobutyryl; or
(c) one R is ethoxycarbonyl and the other R is hydrogen or ethoxycarbonyl; or
(d) one R is isopropoxycarbonyl and the other R is hydrogen or isopropoxycarbonyl.

11. A compound as defined by claim 8, wherein [QC]+ is

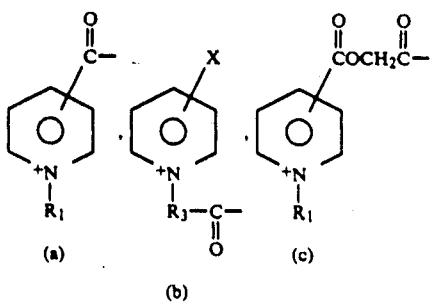

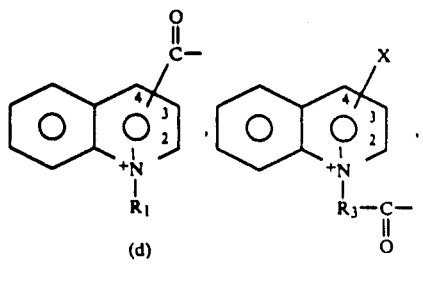

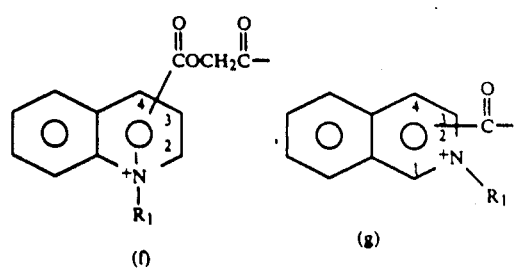

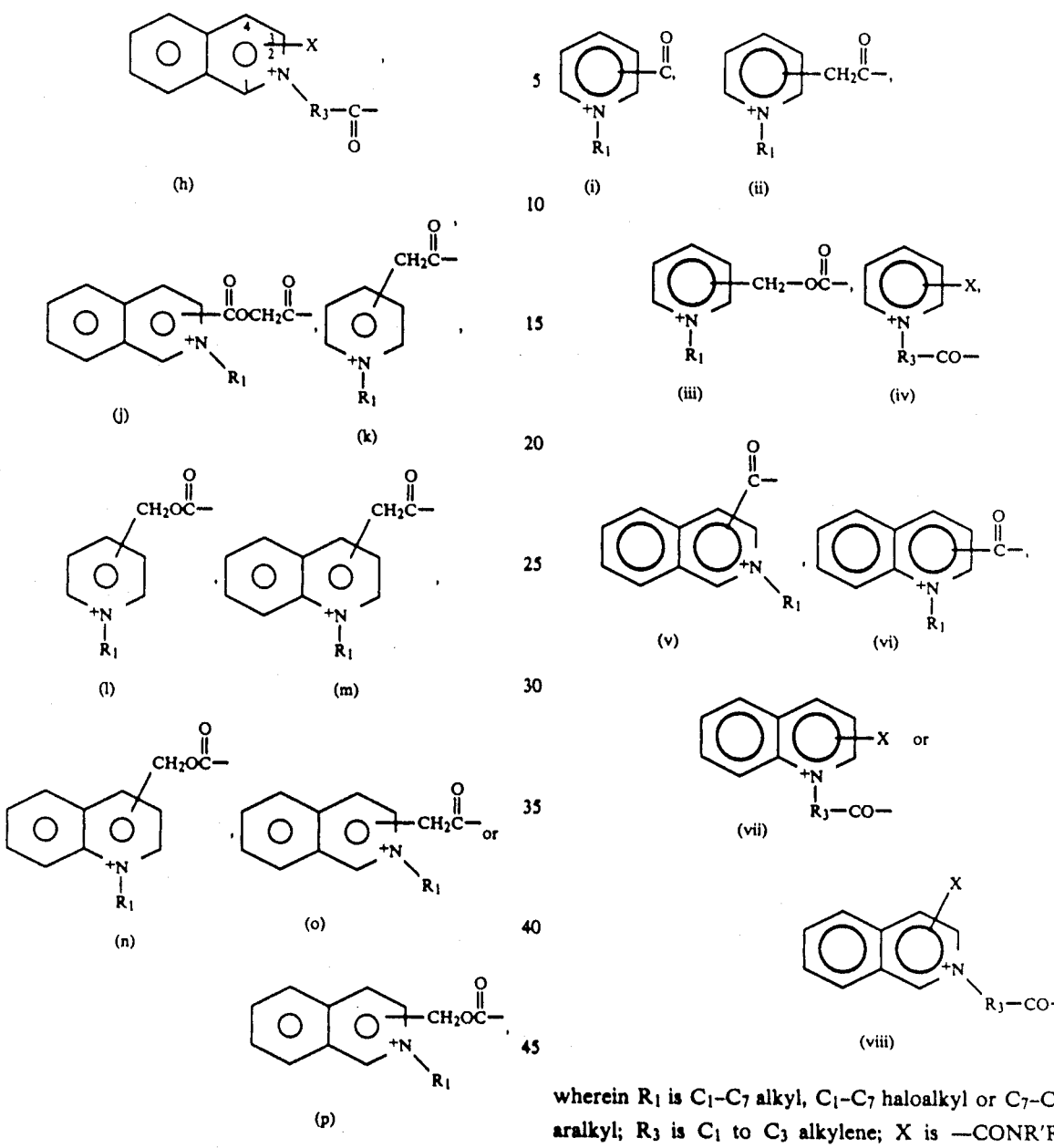

wherein $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a), (c), (k) and (l) and the X substituent in formula (b) can each be attached at the 2, 3 or 4 position of the pyridinium ring; the carbonyl-containing groupings in formulas (d), (f), (m) and (n) and the X substituent in formula (e) can each be attached at the 2, 3 or 4 position of the quinolinium ring system; and the carbonyl-containing groupings in formulas (g), (j), (o) and (p) and the X substituent in formula (h) can each be attached at the 1, 3 or 4 position of the isoquinolinium ring system.

12. A compound as defined by claim 8, wherein [QC]+ is wherein $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (i), (ii) and (iii) and the X substituent in formula (iv) can each be attached at the 2, 3 or 4 position of the pyridinium ring; the carbonyl-containing grouping in formula (vi) and the X substituent in formula (vii) can each be attached at the 2, 3 or 4 position of the quinolinium ring system; and the carbonyl-containing grouping in formula (v) and the X substituent in formula (viii) can each be attached at the 1, 3 or 4 position of the isoquinolinium ring system.

13. A compound as defined by claim 8, wherein [QC]+ is

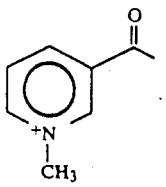

14. A compound as defined by claim 8, having the structural formula

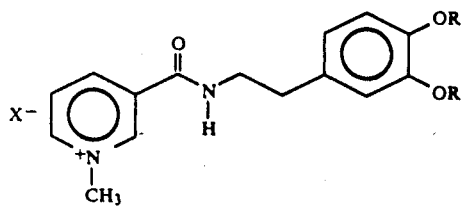

wherein X⁻ is an anion derived from a non-toxic, pharmaceutically acceptable acid.

15. A pharmaceutical composition of matter comprising a compound as defined by claim 1 and a nontoxic pharmaceutically acceptable carrier therefor.

16. A pharmaceutical composition of matter, in unit dosage form, for use in eliciting a dopaminergic response in the brain, said composition comprising:

(i) an amount of a compound as defined by claim 1 sufficient to elicit a pharmacologically effective dopaminergic response in the brain; and
(ii) a non-toxic pharmaceutically acceptable carrier therefor.

17. A pharmaceutical composition as defined by claim 16, said composition being a pharmaceutically acceptable sustained release composition.

18. A method for site-specifically/sustainedly eliciting a dopaminergic response in the brain, comprising administering to an animal in need of such treatment a quantity of a compound as defined by claim 1 sufficient to elicit a pharmacologically effective dopaminergic response in the brain.

19. A method as defined by claim 18, wherein the compound is administered in the form of a pharmaceutically acceptable sustained release composition or wherein the compound is administered via a route of administration capably of slowly releasing the compound into the body.

20. A method for the treatment of Parkinsonism, comprising administering to a patient afflicted with Parkinson's disease a quantity of a compound as defined by claim 1 sufficient to elicit an effective anti-Parkinsonism response.

21. A method for the treatment of hyperprolactinemia or an associate disorder in a patient afflicted with same, comprising administering to said patient a quantity of a compound as defined by claim 1 sufficient to elicit a pharmacologically effective lowering of the prolactin level in said patient.

* * * * *

UNITED STATES PATENT AND TRADEMARK OFFICE
CERTIFICATE OF CORRECTION

PATENT NO. : 4,880,816
DATED : November 14, 1989
INVENTOR(S) : NICHOLAS S. BODOR It is certified that error appears in the above-identified patent and that said Letters Patent is hereby corrected as shown below:

In column 58, claim 3, line 7: delete "ethoxycarbony" and substitute therefor -- ethoxycarbonyl --.

In column 67, in the formula of claim 14 (two occurrences thereof): delete "X-" and substitute therefor -- $X^-$ -- (both occurrences).

In column 67, line 2 of claim 15: delete "nontoxic" and substitute therefor -- non-toxic --.

Signed and Sealed this

Second Day of April, 1991

*Attest:*

HARRY F. MANBECK, JR.

*Attesting Officer*  *Commissioner of Patents and Trademarks*